(12) United States Patent
Blanco et al.

(10) Patent No.: US 11,504,471 B2
(45) Date of Patent: Nov. 22, 2022

(54) SYSTEMS AND METHODS FOR DETECTING DISRUPTIONS IN FLUID DELIVERY DEVICES

(71) Applicant: Diatech Diabetes, Inc., Memphis, TN (US)

(72) Inventors: Luis E. Blanco, Seattle, WA (US); John H. Wilcox, Rockledge, FL (US); Nicholas R. Cooper, Riverview, FL (US); John Clark Gray, Tallahassee, FL (US)

(73) Assignee: Diatech Diabetes, Inc., Memphis, TN (US)

( * ) Notice: Subject to any disclaimer, the term of this patent is extended or adjusted under 35 U.S.C. 154(b) by 879 days.

(21) Appl. No.: 16/382,995

(22) Filed: Apr. 12, 2019

(65) Prior Publication Data

US 2019/0314575 A1  Oct. 17, 2019

Related U.S. Application Data

(60) Provisional application No. 62/656,646, filed on Apr. 12, 2018.

(51) Int. Cl.
*A61M 5/168* (2006.01)
*A61M 5/172* (2006.01)
*A61M 5/50* (2006.01)

(52) U.S. Cl.
CPC ........ *A61M 5/16859* (2013.01); *A61M 5/172* (2013.01); *A61M 5/5086* (2013.01);
(Continued)

(58) Field of Classification Search
CPC .... A61M 2005/16863; A61M 2205/15; A61M 5/16859; A61M 5/172; A61M 5/5086;
(Continued)

(56) References Cited

U.S. PATENT DOCUMENTS

| 4,077,405 | A | 3/1978 | Haerten et al. |
| 5,984,894 | A | 11/1999 | Poulsen et al. |

(Continued)

FOREIGN PATENT DOCUMENTS

| CA | 2921304 A1 | 2/2011 |
| JP | 2004229680 A | 8/2004 |

(Continued)

OTHER PUBLICATIONS

Mossman, John; "Insulin Pumps: Design Basics and Tradeoffs"; EE Times, Power Management Designline; pp. 1-6; May 17, 2010.

*Primary Examiner* — Jason E Flick
(74) *Attorney, Agent, or Firm* — Patterson Intellectual Property Law, P.C.

(57) ABSTRACT

A sensor system capable of detecting tissue counter pressure from patients that utilize infusion pumps to administer their medication is provided. Embodiments include a retrofitted piece that is placed between the user's infusion set and pump, as well as a "smart" infusion set configured for measuring characteristics of a fluid traveling therethrough. Hardware is provided that couples with the sensor to store, analyze, and compare data to distinguish between normal and non-normal injection/infusion profiles. An alert system notifies the user of a malfunction within the pump, within the infusion set, or at the injection/infusion site.

20 Claims, 11 Drawing Sheets

(52) U.S. Cl.
CPC ............. *A61M 2005/16863* (2013.01); *A61M 2205/15* (2013.01)

(58) Field of Classification Search
CPC ...... A61M 2005/2474; A61M 2205/18; A61M 2205/3553; A61M 2205/3569; A61M 2205/581; A61M 2205/582; A61M 5/14244; A61M 5/14248; A61M 5/168; A61M 5/16831; A61M 5/16854; A61M 5/142; A61M 5/24; A61M 5/2455; A61M 5/2466; A61M 5/16836; A61M 5/1723; A61M 2005/1726
See application file for complete search history.

(56) References Cited

U.S. PATENT DOCUMENTS

| | | |
|---|---|---|
| 6,362,591 B1 | 3/2002 | Moberg |
| 6,523,414 B1 | 2/2003 | Malmstrom et al. |
| 6,752,785 B2 | 6/2004 | Antwerp et al. |
| 7,621,893 B2 | 11/2009 | Moberg et al. |
| 7,654,127 B2 | 2/2010 | Krulevitch et al. |
| 7,892,199 B2* | 2/2011 | Mhatre ............. A61M 5/14566 604/65 |
| 8,287,516 B2 | 10/2012 | Komerup et al. |
| 8,346,399 B2 | 1/2013 | Blomquist |
| 8,417,545 B2 | 4/2013 | Galasso et al. |
| 8,449,523 B2 | 5/2013 | Brukalo et al. |
| 8,486,020 B2 | 7/2013 | Hills et al. |
| 8,734,428 B2 | 5/2014 | Blomquist |
| 8,752,436 B2 | 6/2014 | Beck et al. |
| 9,968,742 B2 | 5/2018 | Antwerp et al. |
| 10,201,656 B2 | 2/2019 | Rosinko |
| 2007/0083153 A1 | 4/2007 | Haar |
| 2007/0093753 A1 | 4/2007 | Krulevitch et al. |
| 2009/0069743 A1 | 3/2009 | Krishnamoorthy et al. |
| 2011/0224523 A1* | 9/2011 | Budiman ................ G06F 3/016 345/184 |
| 2016/0310663 A1* | 10/2016 | Dantsker ........... A61M 5/31571 |
| 2016/0361491 A1 | 12/2016 | Shaked et al. |
| 2017/0181894 A1* | 6/2017 | Allen ...................... F04B 43/04 |
| 2018/0071450 A1 | 3/2018 | Ruhland |

FOREIGN PATENT DOCUMENTS

| | | |
|---|---|---|
| JP | 2016535607 A | 11/2016 |
| WO | 2009109344 A1 | 9/2009 |
| WO | 2010059588 A1 | 5/2010 |

* cited by examiner

SYSTEMS AND METHODS FOR DETECTING DISRUPTIONS IN FLUID DELIVERY DEVICES

CROSS-REFERENCE TO RELATED APPLICATION

This application claims the benefit of, and priority to, U.S. Provisional Patent Application Ser. No. 62/656,646, filed Apr. 12, 2018, the entirety of which is incorporated by reference herein and commonly owned.

FIELD OF THE INVENTION

The present invention generally relates to systems and methods for measuring characteristics of a fluid flow, and in particular, systems and methods for measuring characteristics of a fluid flow associated with an infusion pump system.

BACKGROUND

Infusion pumps may be powered electrically or mechanically. Different pumps operate in different ways. In a syringe pump, fluid is held in the reservoir of a syringe, and a moveable piston controls fluid delivery. In an elastomeric pump, fluid is held in a stretchable balloon reservoir, and pressure from the elastic walls of the balloon drives fluid delivery. In a peristaltic pump, a set of rollers pinches down on a length of flexible tubing, pushing fluid forward. In an electrokinetic pump, an electrokinetic engine delivers electric potentials across an electrokinetic porous media, causing the electrokinetic solution with the engine to displace a movable partition initiating fluid delivery.

Insulin pump injections are administered to counteract a buildup of glucose in the blood after food ingestion and is thus administered many times in a single day through a cannula that is replaced every three days. Conversely, dual-hormone infusion pumps exist where medication is given to raise glucose levels and lower them through a combination of medicaments such as glucagon and insulin. Eventually, however, repeated needle/cannula insertions and chronic insulin exposure compromise the small patches of skin to which patients attach their pumps and infusion sets. This inevitably results in adverse outcomes for the insulin device, giving rise to various malfunctions.

As of 2018, an estimated five hundred and fifty thousand Americans with diabetes use a combination of specialized insulin pumps to manage their blood glucose levels. However, many Type I diabetic patients have reported malfunctions with their pumps and infusion sets, such as improper needle/cannula insertion into the skin, the development of kinks in the infusion cannula, blockages within the cannula, medicine leakage from the injection/infusion site, and/or issues with injections sites such as lipohypertrophy, scar tissue, infection, bleeding, bruising, pain, adhesive problems, and irritation. These malfunctions can severely hinder or completely halt the life-saving function of the device and lead to hazardous consequences to those living with this disease.

Therefore, it will be advantageous to provide a system that can detect malfunctions within an infusion pump system and notify the user and/or some third person of these malfunctions.

SUMMARY

Many advantages will be determined and are attained by one or more embodiments of the technology, which in a broad sense provides an apparatus and methods for detecting one or more malfunctions related to an infusion pump such as an insulin pump.

A sensor system is provided that actively monitors a pump's performance and fluid delivery in order to detect one or more changing conditions at the infusion site that indicate partial or total delivery failure of the fluid. One or more indicators may be provided for generating an audio, visual, text and/or email notification. The sensor may be incorporated into an adjunct device, such as a sensor housing as herein described, which connects to a conventional and/or new pump or may be integrated as part of a new pump and/or infusion set design. The sensor may provide diagnostic capabilities for the pump, the infusion site, and infusion set and provide user alerts about failed injections/infusions, decreasing pump performance, degradation of an infusion site, infusion set failures, and may predict delivery failure based on any abnormalities detected by the system related to historic performance of the pump, infusion set and infusion site. This technology may improve safety and performance of the pump system and decrease or eliminate waste caused by failed injections/infusions (e.g. extra insulin or replacement pumps or infusion sets).

One or more embodiments disclosed herein relate to a "smart" infusion set capable of collecting/logging data on the medication being delivered to a patient. Embodiments include enhanced data collecting features through the utilization and incorporation of an integrated sensor and tubing infusion set. Applications of the embodiments disclosed herein include detecting tissue counter pressure (TCP), the fluid back pressure exerted by infused tissue, in patients who utilize insulin pumps to administer their medication. An infusion set within the diabetes industry may include a replaceable portion of an insulin pump system that incorporates tubing, adhesive, and an injectable cannula that allows insulin or other medication or fluid to be delivered intradermally or subcutaneously.

Sensors used in connection with the various embodiments disclosed herein ideally have high sensitivity capable of detecting pressure differences of less than 0.1 psi. Other sensitivity ranges, however, are considered to be within the scope of the present disclosure. Hardware and/or software may couple with a sensor and make it possible to store data to characterize and distinguish between normal and non-normal, or aberrant, injections/infusions. An alert system may be employed to notify the patient/user of malfunctions associated with the infusion pump, infusion set, or the infusion site, including but not limited to: blocks in the flow line; occlusions at the medication reservoir, pump, or infusion site; leaks at the infusion site due to cannula displacement; or from perforations of the tubing, reservoir, and/or cannula.

Embodiments disclosed herein are able to determine when an injection/infusion site malfunction is occurring in real time during, but not limited to, insulin deliveries using an insulin pump. These malfunctions can be defined as, and are not limited to: leakages; blockages; kinking of the cannula that impedes medication flow; dislodgement of the cannula from the injection site; and overall dislodgement of the infusion set from the body. The "smart" infusion set also distinguishes between healthy and unhealthy tissue that is being infused with medication using an algorithm that considers a patient's previous and current datasets gathered from an in-line sensor.

Embodiments of the systems and methods disclosed herein include and/or utilize an operational algorithm that develops and/or analyzes trends based off each patient's medical infusion process and set limits on parameters including, but not limited to, initial injection tissue counter pressure, maximum and minimum tissue counter pressure after beginning infusion, maximum and minimum tissue counter pressure rate, time to maximum tissue counter pressure, and time to steady state value after bolus event. If the sensor values are outside predefined limits, then the product will alert user via at least one of an audio, visual, and Bluetooth™ message to a mobile device application. Various embodiments are able to pair with a mobile application on a smartphone wherein a patient will be able to log what injection site they are using before each injection and have an alert sent to them when a malfunction is going to occur with their infusion technology. The mobile application can take or receive alerts and recommend the use of a different infusion set and/or a different infusion site for the patient. The mobile application can use data set trends to identify and map key injection sites that have had recurring malfunctions.

Embodiments disclosed herein are able to quickly detect malfunctions at the insertion site of medication or fluid delivery and alert the user to these malfunctions. In addition, one or more embodiments are configured to educate infusion pump users on areas of unhealthy and healthy tissue to increase the efficacy of the medication on the user when inserting into new sites. One or more embodiments may also be used as a diagnostic tool to understand any physiological changes at the site of infusion including, but not limited to, lipohypertrophy, lipoatrophy, scar tissue, and other damaged or inflamed tissue that may result from daily use of insulin and continuous subcutaneous infusion/injection of medication.

In one or more embodiments, the sensor is combined with the tubing of the infusion set as one continuous piece. Medication is able to flow through a sampling chamber where the sensor is connected and reads the in-line pressure as the medication flows, as well as the tissue counter pressure created once the medication goes into the patient. In one or more embodiments, data collected by the sensor system during infusion pump medication deliveries are monitored by a microcontroller, and any abnormal data points that arise from malfunctions result in an alert sequence that turns on an audio and/or LED light. In one or more embodiments, a Bluetooth™ message is sent to the patient's mobile device that would already be paired to the system before injection of medication. Once a user is notified about a malfunction via Bluetooth™ alert or SMS messaging or an external device (smart watch, Fitbit, etc), the mobile application promptly suggests to the patient that they observe their infusion site and re-inject into a new location.

One or more embodiments of the invention disclosed herein introduce the ability to measure tissue counter pressure (TCP) via an inline fluid pressure sensor. A programmatic basis (computer algorithm) for making decisions based on TCP readings is also disclosed. One or more embodiments include a custom chassis configured for housing electronics as a modular add-on to an existing infusion pump make and model. Certain embodiments are able to use TCP analytics to detect when a patient is likely to experience a failure of medication delivery (predictive and preventative); detect when a leak or block in the injection site or infusion set has developed; provide distinctive alerts to the patient for different symptoms based on these readings (e.g. distinguishing blockages or leaks); and recording this data for patient and doctor records (with the ability to tune the sensitivity of the invention based on the history of TCP readings on a given injection site). In one or more embodiments, the analytics are coupled with a mobile device application to identify infusion sites for the patient to use in the future and infusion sites for the patient to avoid because of recurring malfunction history. While the chassis exists in order to make the invention backwards compatible with current infusion pump models, integration into the main housing of a manufactured pump and/or infusion set does not require this or other pieces to interact in the same way, although the overall features and advantages remain the same.

Advantages of the embodiments of the present disclosure over the prior art include, but are not limited to, providing an infusion set having "smart" capabilities (i.e. pressure readings/flow readings) that can provide analytics based on tissue characteristics; detecting the presence of abnormal tissue from fluid flow measurements and characteristics; evaluating whether or not medication has flowed into the patient from a mechanical perspective; providing analytics on tissue being injected into; identifying medication leaking from infusion site; identifying blockages at an infusion site; identifying poor medication flow associated with a displacement of an infusion cannula; notifying a patient if a malfunction is likely to occur based on data acquired from said patient or extrapolated from a population; notifying a patient when a malfunction is occurring; and logging and showcasing incidents of malfunctions for healthcare providers via a data management platform like those used for patients with diabetes.

The technology will next be described in connection with certain illustrated embodiments and practices. However, it will be clear to those skilled in the art that various modifications, additions and subtractions can be made without departing from the spirit or scope of the claims.

BRIEF DESCRIPTION OF THE DRAWINGS

For a better understanding of the technology, reference is made to the following description, taken in conjunction with any accompanying drawings in which.

DETAILED DESCRIPTION OF EMBODIMENTS

Figure 1A:
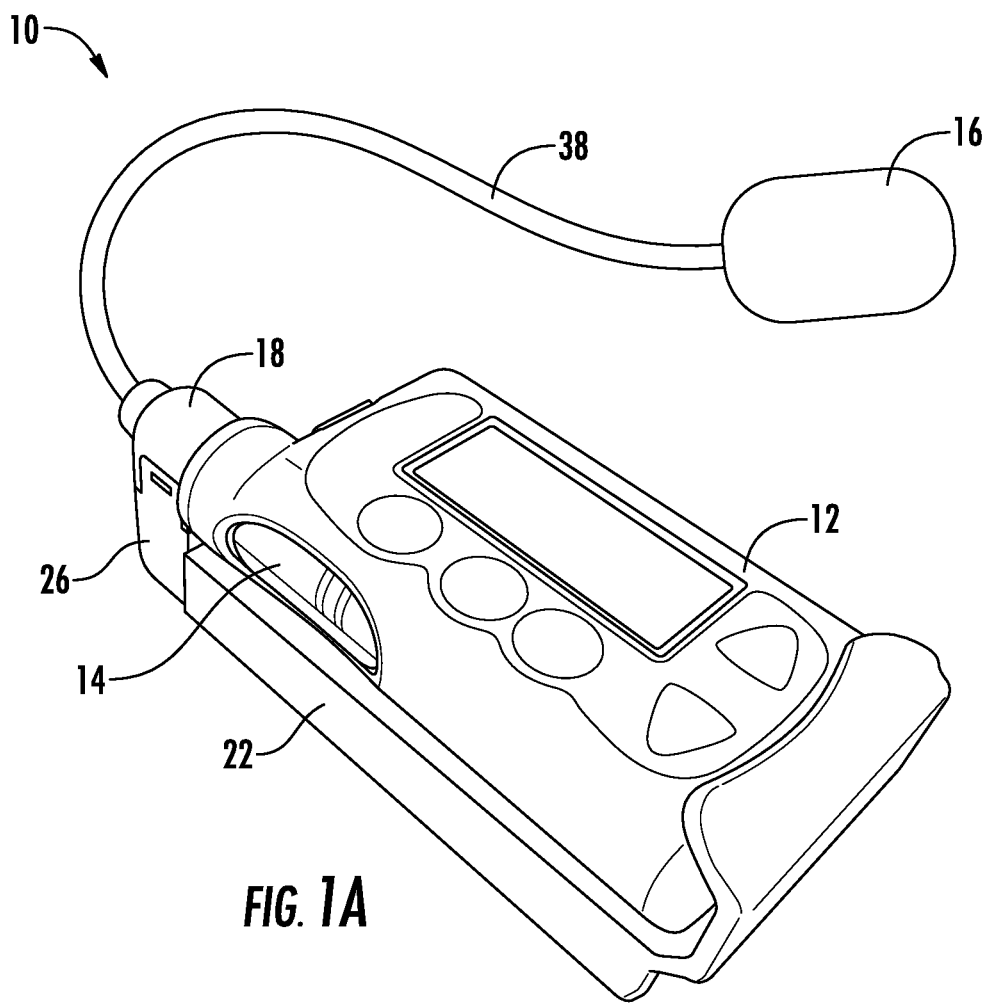
FIG. 1A depicts an exemplary system in accordance with the teachings of the present disclosure.

Embodiments of the present invention will now be described more fully hereinafter with reference to the accompanying drawings, in which embodiments of the invention are shown by way of illustration and example. The invention may, however, be embodied in many forms and should not be construed as limited to the embodiments set forth herein. Rather, these embodiments are provided so that this disclosure will be thorough and complete, and will fully convey the scope of the invention to those skilled in the art.

Exemplary System

Discussion of an embodiment, one or more embodiments, an aspect, one or more aspects, a feature, one or more features, or a configuration or one or more configurations is intended to be inclusive of both the singular and the plural depending upon which provides the broadest scope without running afoul of the existing art and any such statement is in no way intended to be limiting in nature. Technology described in relation to one or more of these terms is not necessarily limited to use in that embodiment, aspect, feature or configuration and may be employed with other embodiments, aspects, features and/or configurations where appropriate.

One or more embodiments of the present disclosure provide a sensor that actively monitors a pump's performance and fluid delivery in order to detect changing conditions at the infusion site that indicate insulin delivery failure.

With reference initially to FIGS. 1A-3, one or more embodiments of the present disclosure comprise systems and methods for at least one of monitoring characteristics of a fluid being delivered to a subject and detecting abnormalities and/or malfunctions within a fluid delivery system (such as, for example, an insulin pump or other device), within an infusion set, and/or at an infusion site of a subject. One or more embodiments of the system 10 comprise (i) a pump 12 configured for delivering a fluid (such as, for example, insulin or other medicament or fluid); (ii) an infusion set 16 in fluid communication with the pump and configured for infusing a subject with the fluid; (iii) a sensor housing 18 providing a sensor 20 selectively coupled between the infusion pump 12 and the infusion set 16; and (iv) an electronics kit 22 configured for powering the sensor via an electrical connection 24 therebetween and analyzing and/or transmitting data collected from the sensor 20. Alternatively, the sensor 20 and/or sensor housing 18 may be incorporated entirely within a pump design (not shown) without departing from the spirt and scope of the present disclosure. Likewise, the electronics configured for receiving, storing, and/or analyzing data from the sensor may be housed within the pump itself. In one or more embodiments, the sensor and/or the associated electronics may be utilized to perform diagnostics on the injection site in order to monitor the performance of the infusion set, assess the health of the tissue, evaluate the viability of the infusion site, detect failed injections, detect infusion set malfunctions, monitor pump performance, and predict delivery failure based on any abnormalities detected by the system related to historic performance of the pump, infusion set, and infusion site.

In one or more embodiments, the pump 12 may comprise an infusion pump such as an insulin pump. However, other suitable pumps are considered to be within the scope of the present disclosure. Moreover, one of ordinary skill in the art having the benefit of the teachings of the present disclosure will appreciate that the sensor systems and methods disclosed herein may also be used in connection with other types of fluid delivery devices, such as, for example, a handheld syringe, intra-venous fluid delivery systems, or medication injection pens without departing from the spirit and scope of the claims.

In one or more embodiments, the sensor 20 is configured for at least one of collecting and transmitting data pertaining to the fluid pressure. The data may be transmitted to and received by a secondary device, such as the electronics kit or other secondary device configured for receiving the data. Once a failure or malfunction is detected, an alert may be activated which indicates to the user and/or some third party that a problem exists. The alert may be an audio, visual, tactile, and/or message response (e.g. text and/or email) that originates from any suitable component of the system, including but not limited to the sensor, the pump, the sensor housing, the electronics kit, the infusion set, or other device. The sensor 20 may be electrically connected, either directly or by way of the electronics kit, to a Wi-Fi, radiofrequency, and/or Bluetooth™ transceiver and/or to other wireless type systems for communicating with a remote device such as a phone, watch, tablet, or computer to provide the alert. Alternatively, the alert may be provided by at least one of the sensor and the electronics kit.

With continued reference to FIGS. 1A-3, one or more embodiments of the system 10 comprise a sensor housing 18 coupled on a first end to an infusion pump 12 and on a second end to an infusion set 16 configured for delivering a medicament or other fluid to a subject (such as a patient or a user). The electronics for measuring and analyzing changes in pressure detected by the sensor may be confined within an electronics housing, or kit 22, which is connected to the sensor within the sensor housing via an electrical connection 24. The electrical connection may incorporate any type of connecter (e.g. gold, silver, etc.) which connects the sensor housing with the electronics kit. Alternatively, the sensor housing 18 and/or the pump or infusion set may have all necessary electronics needed to measure and analyze changes in pressure or other fluid characteristics detected by the sensor.

In one or more embodiments, the electronics kit 22 may be sized and shaped to cradle the infusion pump for ease of use and handling. To protect the electrical connection from disruption, a wire housing 26 may be provided, which removably connects to the sensor housing by way of a suitable connector portion 28.

Exemplary Sensor Housing

As depicted in FIGS. 4-10, one or more embodiments of the systems and methods disclosed herein comprise a sensor housing 18 having a first, or upper, connector portion 30 configured for connecting the sensor housing to the infusion set and a second, or lower, connector portion 32 configured for connecting the sensor housing 18 to the pump 12. An interior portion of the sensor housing provides a sampling chamber 34, or cavity, in fluid communication with the first and second connector portions 30, 32, which defines the location within the sensor housing 18 where characteristics of the fluid passing therethrough are measured and/or analyzed by the sensor 20. Alternatively, the sampling cavity my protrude from, or reside exterior to, a body portion of a sensor housing without departing from the scope of the present disclosure. In the exemplary embodiments disclosed herein, a sensor chamber 36 is accessible from the exterior of the sensor housing 18, thereby enabling convenient placement and/or maintenance of the sensor 20 for measuring a fluid pressure or other fluid characteristic in said sampling cavity 34.

Figure 1B:
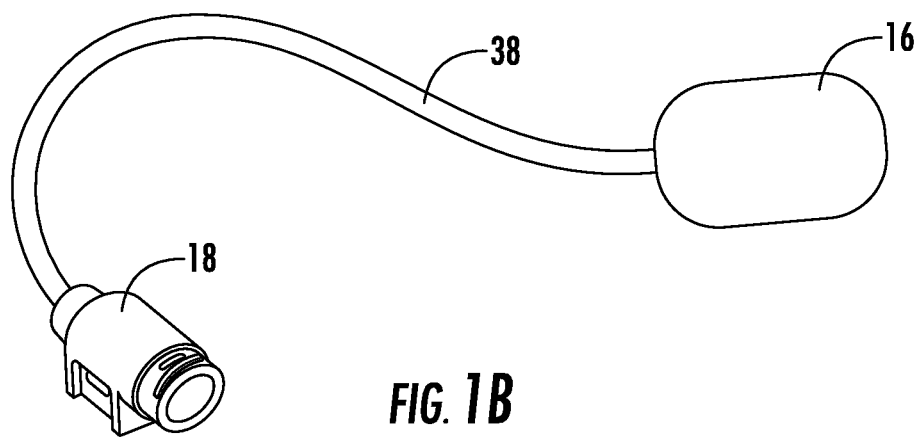
FIG. 1B depicts an exemplary "smart" infusion set in accordance with the teachings of the present disclosure.
Figure 2:
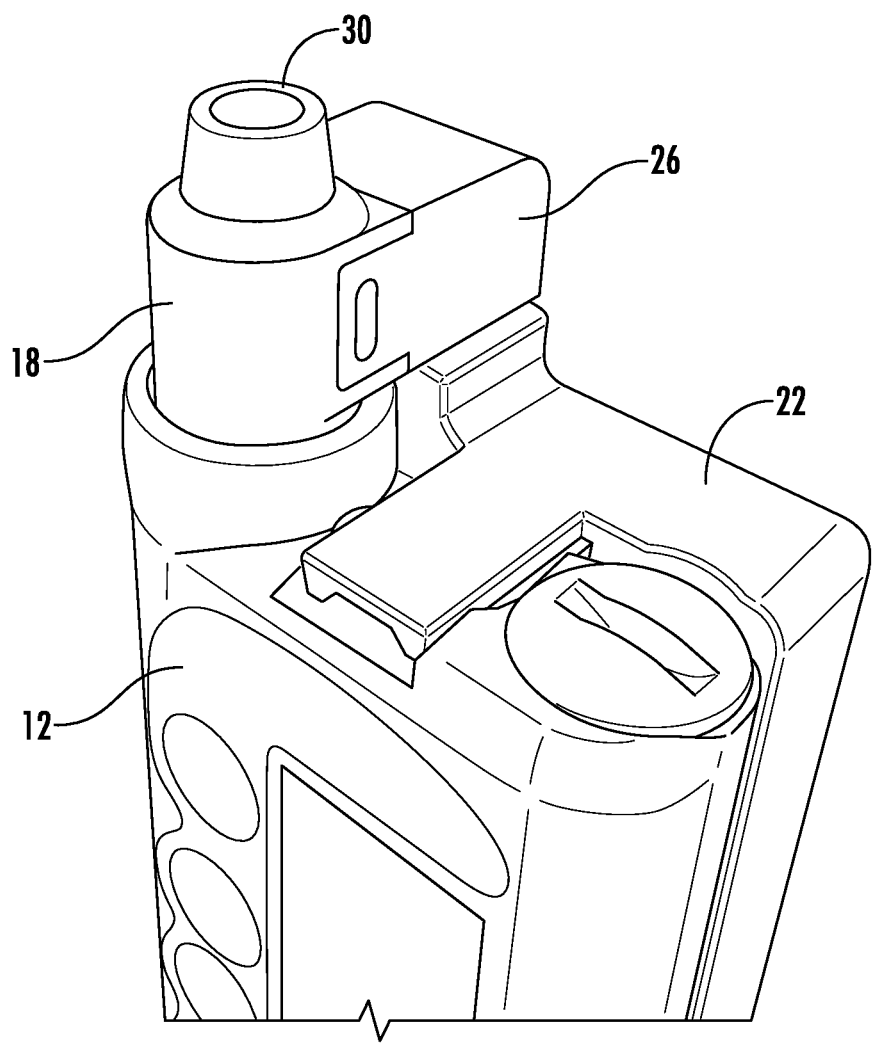
FIG. 2 depicts an exemplary system in accordance with the teachings of the present disclosure.
Figure 3:
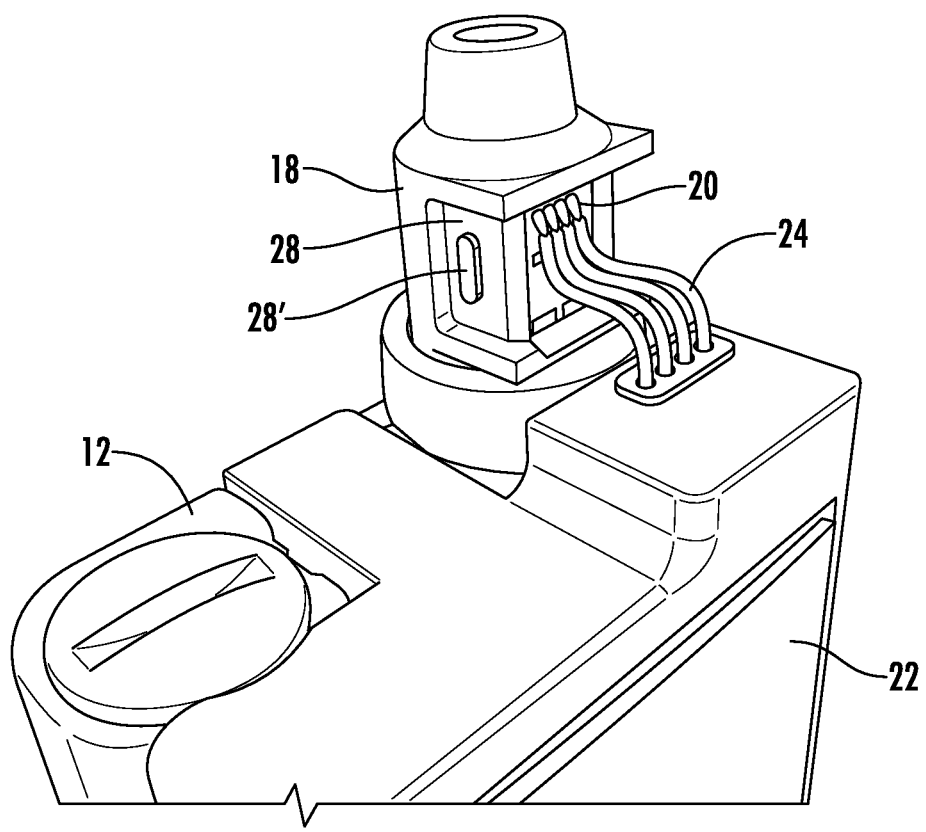
FIG. 3 depicts an exemplary system in accordance with the teachings of the present disclosure.
Figure 4:
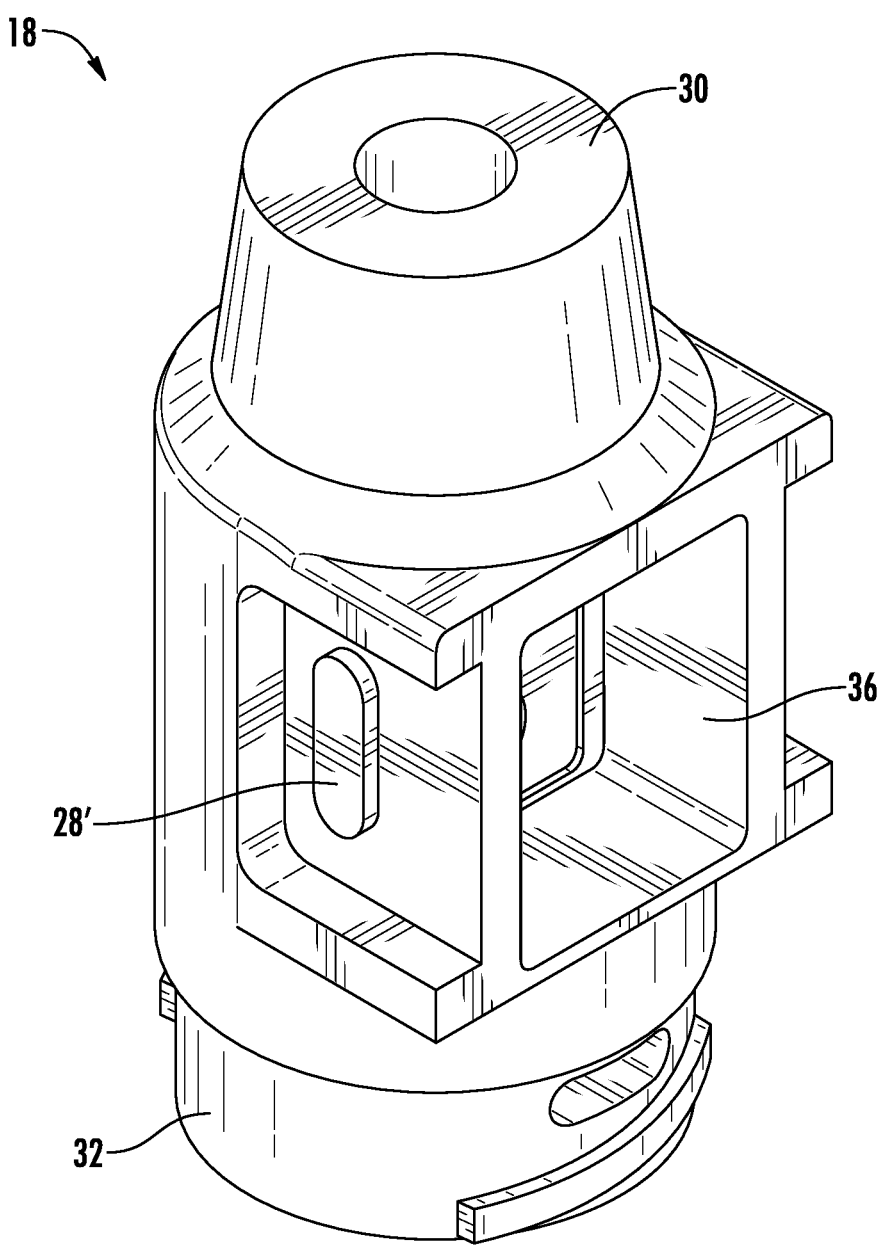
FIG. 4 depicts a perspective view of exemplary sensor housing.
Figure 6:
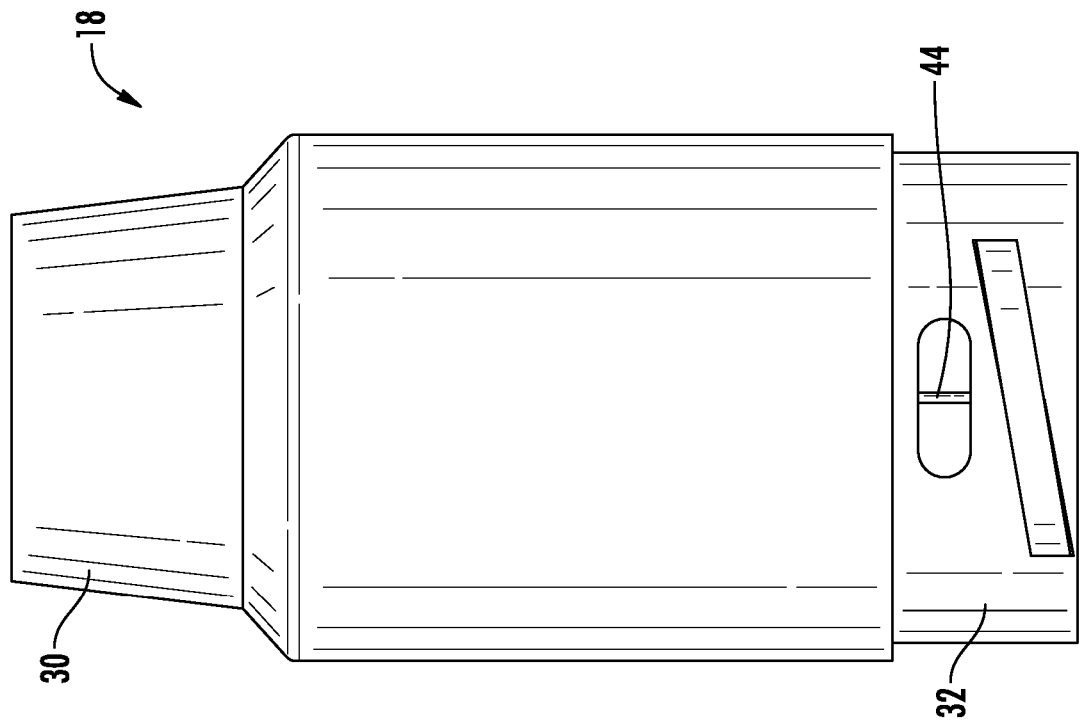
FIG. 6 depicts a rear view of an exemplary sensor housing.

The first connector portion 30 may be connected to a tube 38 associated with an infusion set 16 so as to provide the fluid to the subject (see, e.g., FIG. 1). Tubeless embodiments, however, are envisioned. The tube 38 may connect to the first connector portion 30 using any suitable connecting means including, but not limited to, a threaded connection, a luer-type connection, a magnetic connection, and/or an adhesive, such as a suitable gluing composition or other permanent or semi-permanent connection. In an alternative embodiment, such as the embodiment of FIG. 1B, the sensor housing 18 may be an integral component of a unitary infusion set, wherein the tubing 38 is permanently affixed to the first connector portion 30 on one end and the patient interface of the infusion set 16 on the other end. In one or more embodiments, the tubing 38 is formed from polyurethane medical tubing. However, other suitable materials, including but not limited to plastics, hypoallergenic materials, and chemically stable materials, are within the scope of the present disclosure.

Likewise, the second connector portion 32 may be connected to the pump 12 using any suitable connecting means, including but not limited to a threaded connection, a luer-type connection, a magnetic connection, and an adhesive, such as a suitable gluing composition, so long as the second connector portion 32 is placed in fluid communication with the fluid reservoir 14 within the pump 12 so as to permit the flow of fluid through the sensor housing 18. As will be apparent to one of ordinary skill in the art having the benefit of the teachings of the present disclosure, any means of connecting the first and second connector portions to the infusion set and pump, respectively, should be water and air tight so as to enable accurate measurements by an incorporated sensor.

Figure 12:
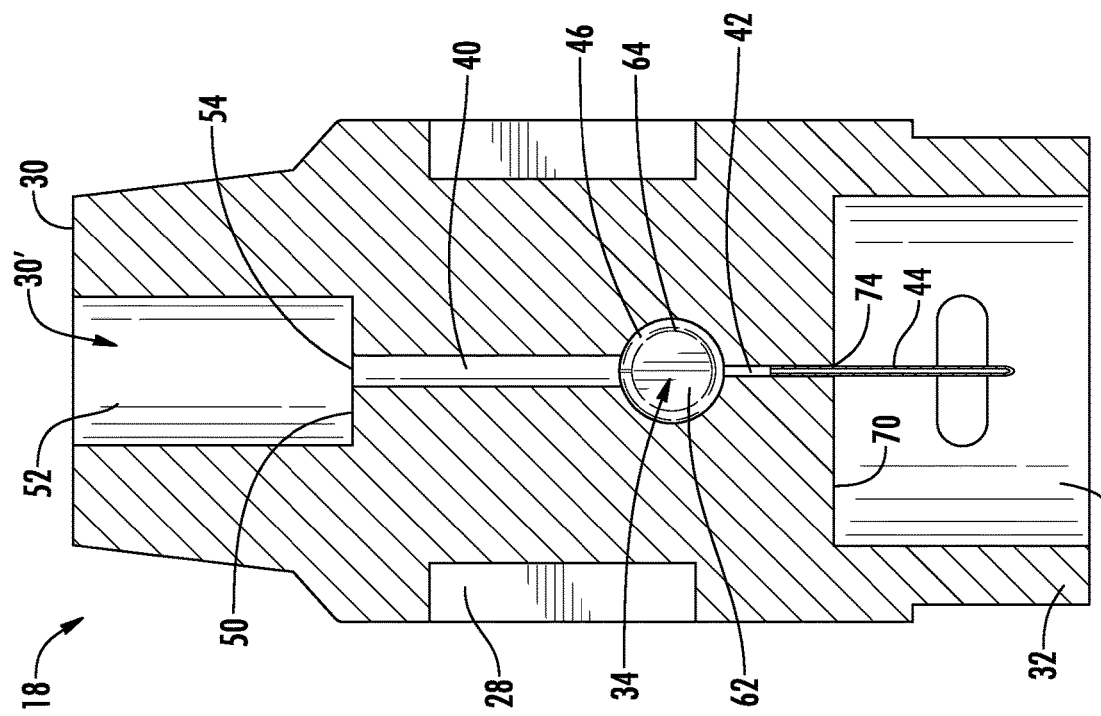
FIG. 12 depicts a front cross-sectional view of an exemplary sensor housing.
Figure 11:
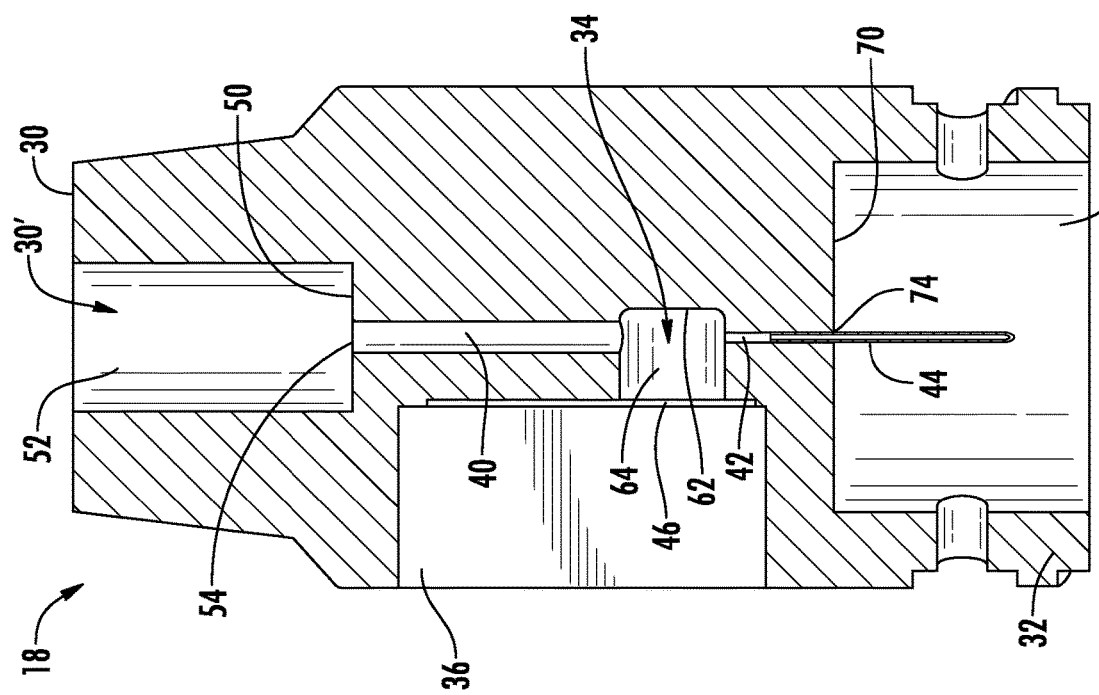
FIG. 11 depicts a side cross-sectional view of an exemplary sensor housing.
Figure 13:
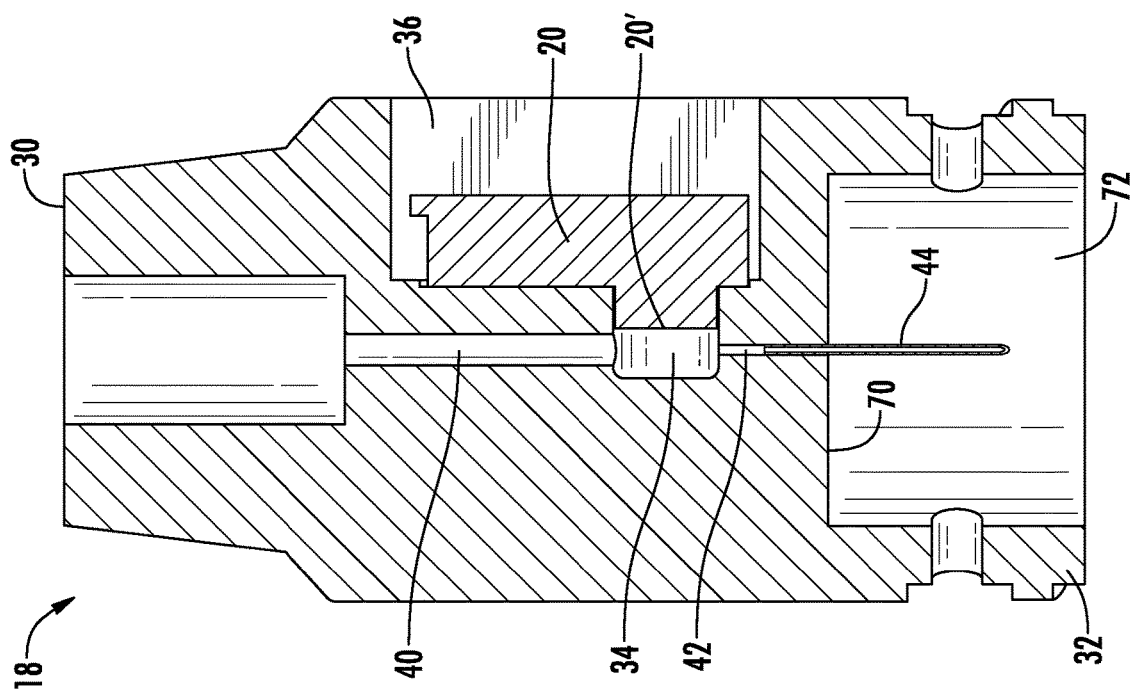
FIG. 13 depicts a second side cross-sectional view of an exemplary sensor housing.

Referring now to FIGS. 11-13, which depict cross-sectional views of the exemplary sensor housing 18 of FIGS. 1A-10, one or more embodiments of the systems and methods disclosed herein comprise a sensor housing 18 having a first connector portion 30 configured for connecting the sensor housing 18 to the infusion set 16 and a second connector portion 32 configured for connecting the sensor housing 18 to the pump 12. A sampling cavity 34 may be positioned in-line between the first connector portion 30 and the second connector portion 32. In one or more embodiments, the sampling cavity 34 is in fluid communication with the first 30, or upper, and second 32, or lower connector portions via first 40 and second 42 channels, respectively. Embodiments devoid of first and second channels, however, are within the scope of the present disclosure. The first 40 and second 42 channels may provide a path for first and second needles 44, respectively. However, embodiments having only one needle 44 positioned within at least one of the first 40 and second 42 channels, as well as embodiments devoid of any needles, are considered to be within the scope of the present disclosure. As described above, a sensor chamber 36 in fluid communication with the sampling cavity 34 may also be provided, wherein said sensor chamber 36 may be configured for accommodating the sensor 20 for measuring a fluid pressure or other fluid characteristic in said sampling cavity 34. One or more embodiments may employ a medical pressure sensor, such as a NovaSensor NPC-120 sensor, that has pressure detecting capabilities relative to the pressures within the insulin or other pump. Other sensors, however, are considered to be within the scope of the present disclosure, such as, but not limited to, a piezoelectric sensor, or a sensor configured for detecting at least one of voltage, current, electrochemical variations, optical, ultrasonic, or any other desirable characteristic.

In one or more embodiments, a needle 44 positioned within, adjacent to, and/or in fluid communication with the second, or lower, channel 42 pierces a fluid reservoir 42 of an insulin or other pump so as to enable a flow of fluid through the sensor housing 18. Stand-alone fluid reservoirs apart from a pump may also be utilized and engaged by the sensor housing. In one or more embodiments, the sensor housing 18 may be screwed onto the pump 12 with a twist and lock movement such that it is compatible with conventional insulin pumps that utilize tubing. In one or more embodiments, this twist and lock movement drives the needle 44 present in the lower portion of the sensor housing into a reservoir 14 of the pump 12, enabling the flow of fluid through the needle 44. This configuration may allow medication or other fluid to flow to the sensor 20 for detection of pressure or other changes or characteristics in the fluid. The sensor 20 may be located anywhere between the pump's medication reservoir and the tubing. In other embodiments, the sensor may be located anywhere between the pump and user. Medication or other fluid may flow through the sensor and pressures or other characteristics may be detected by, for example, an NPC-120 pressure monitor that is within the fluid pathway of the sensor.

In one or more embodiments, data collected by the sensor 20 during insulin pump medication deliveries may be monitored and/or analyzed by the sensor and/or the electronics kit, and any abnormal signals may result in an alert sequence. By registering pressures that are abnormal when compared to normal medication delivery sequences, the sensor can detect a malfunction associated with either the pump, infusion set or infusion site, as well as insulin pump blockages or leakages at the infusion site. Once the user is notified about a malfunction, they may be prompted to observe their infusion site and reinject their infusion kit into a new location. In one or more embodiments, the system may identify a suitable reinjection site for the user based on, for example, data in the system pertaining to prior fluid deliveries.

One or more embodiments of the sensor housing 18 have a first connector portion 30 configured for connecting the sensor housing 18 to an infusion set and a second connector portion 32 configured for connecting the sensor housing 18 to a pump 12. A sampling cavity 34 may be positioned between the first connector portion 30 and the second connector portion 32, wherein the sampling cavity 34 is in fluid communication with the first and second connector portions via first 40 and second 42 channels, respectively. As described above, however, embodiments devoid of first and second channels are envisioned. In one or more exemplary embodiments, the first 40 and second 42 channels are configured for providing a path for first and second needles 44, respectively. In other embodiments, only one of either the first and second channels are configured for receiving a needle 44. Embodiments devoid of needles are also envisioned. The sensor housing 18 may further comprise a sensor chamber 36 in fluid communication with the sampling cavity 34, said sensor chamber 36 configured for accommodating a sensor 20, wherein said sensor 20 measures a characteristic or property of the fluid in the sampling cavity 34.

In one or more embodiments, the sensor chamber 36 extends orthogonally to a flow path of fluid through the first 40 and second 42 channels. However, orientations other than orthogonal are envisioned, including originations greater than or less than 90 degrees. In one or more embodiments, the sensor chamber 36 houses the body of an incorporated sensor 20, and enables a sensing portion 20' of a sensor 20 to engage fluid in the sampling cavity 34 through an aperture 46 formed in a portion of the sampling cavity 34. Embodiments devoid of a sensor chamber are also within the scope of the present disclosure. For instance, the body portion of a sensor 20 may be located remote from a sensing portion 20'.

In one or more embodiments, a tube 38, or other fluid channel, is connected to the first connector portion 30 on one end and an infusion set 16 on the other end, thereby enabling the delivery of a fluid to a subject. Tubeless embodiments are also envisioned.

The sensor 20 may be configured for at least one of collecting and transmitting data pertaining to the fluid, including but not limited to, fluid pressure, flow rate, viscosity, composition, pH, temperature, conductivity, impedance, fluorescence, absorbance, and/or the presence of absence of said fluid in the sampling cavity 34.

Figure 5:
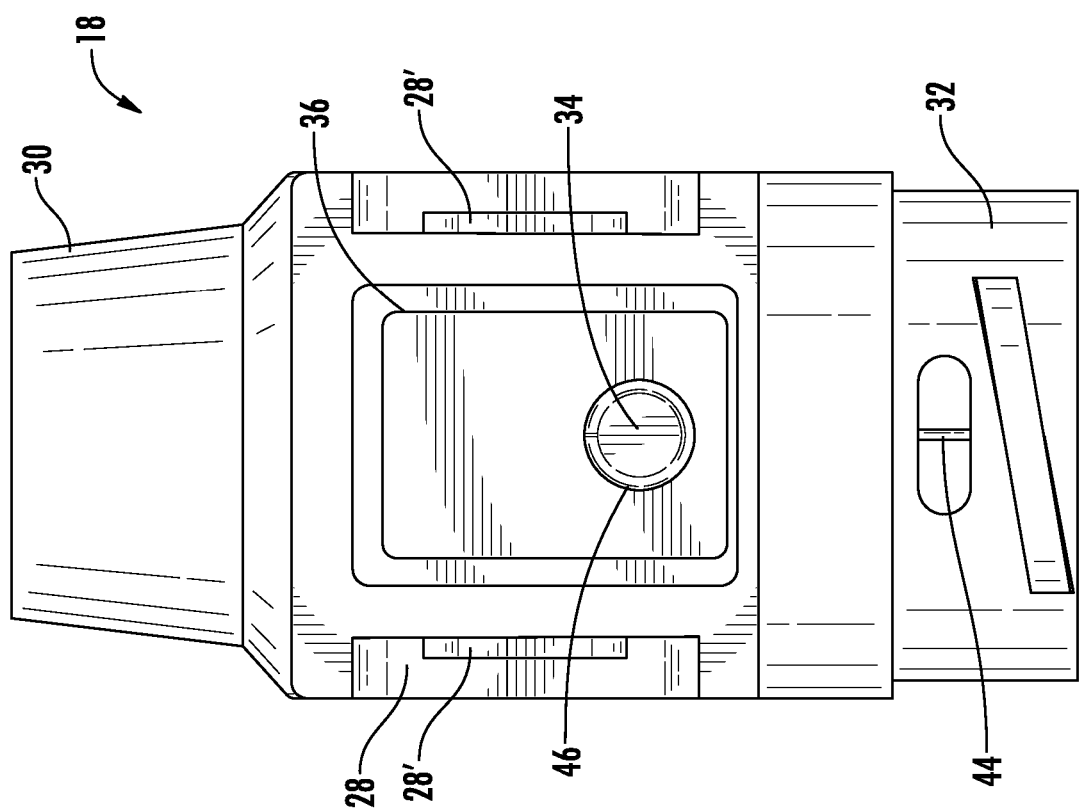
FIG. 5 depicts a front view of an exemplary sensor housing.
Figure 8:
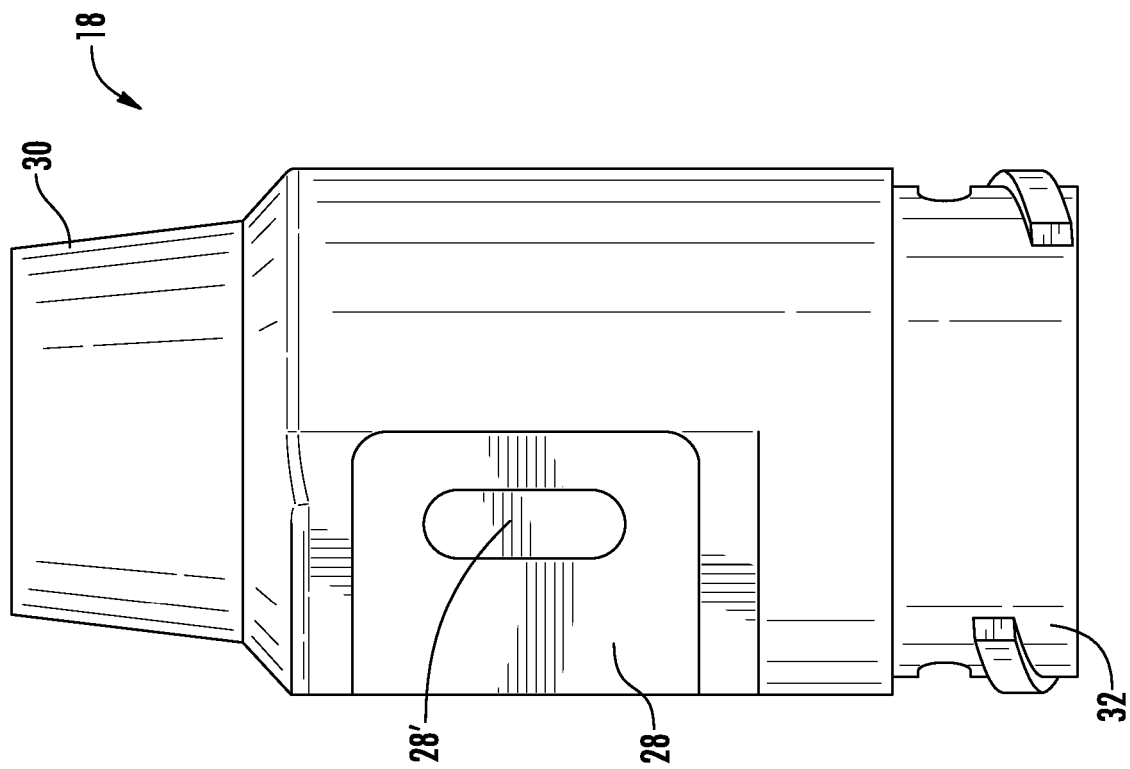
FIG. 8 depicts a second side view of an exemplary sensor housing.
Figure 7:
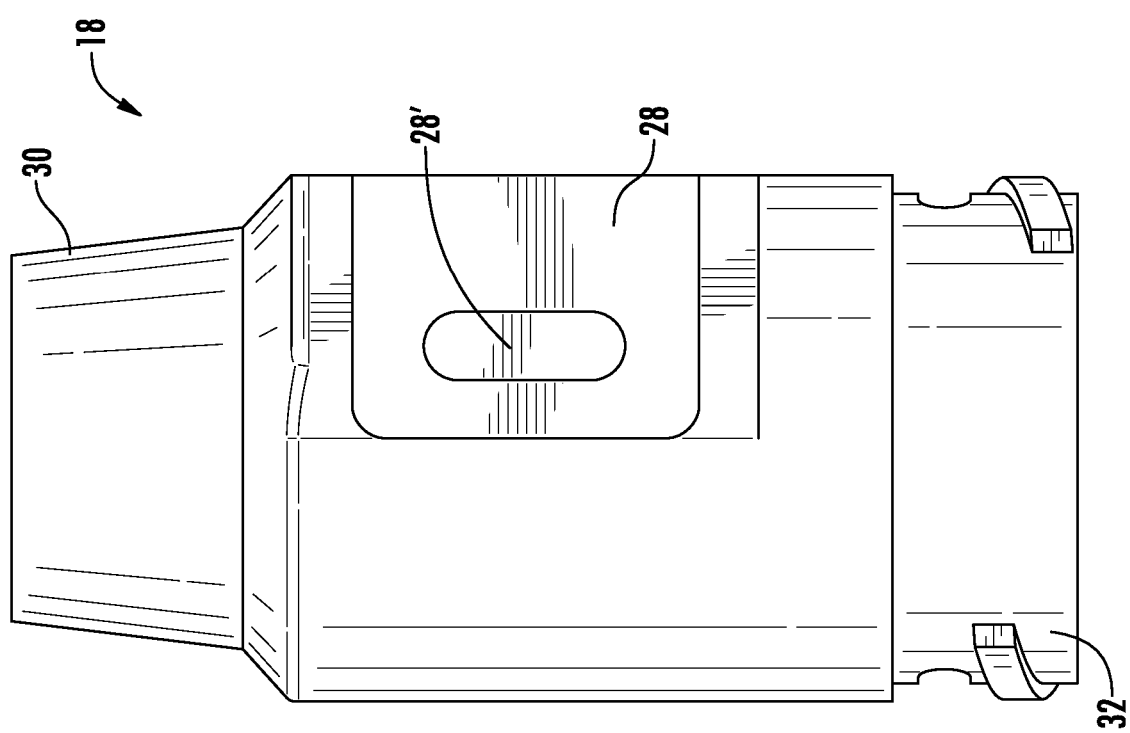
FIG. 7 depicts a first side view of an exemplary sensor housing.
Figure 9:
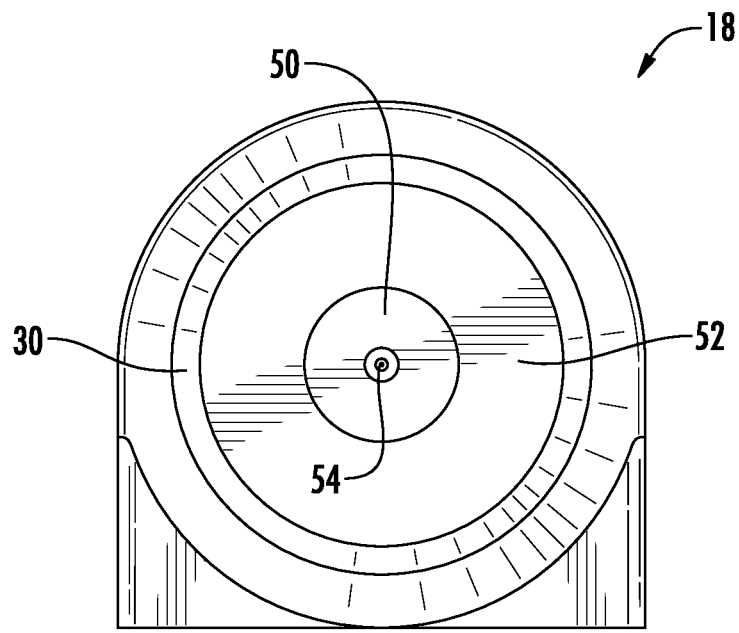
FIG. 9 depicts a top view of an exemplary sensor housing.
Figure 10:
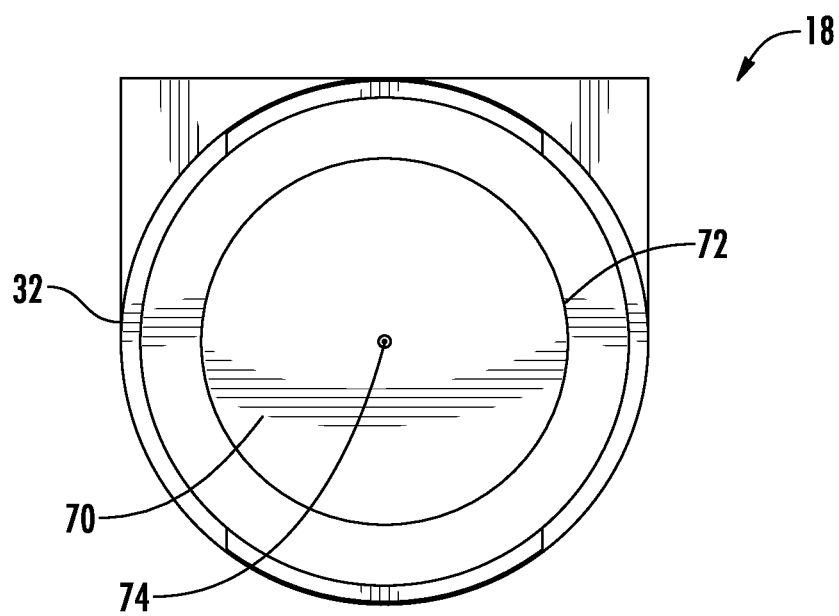
FIG. 10 depicts a bottom view of an exemplary sensor housing.

In one or more embodiments, a portion of the sampling cavity 34 is defined by a portion of the sensor 20, such as, for example, a sensing portion 20' of the sensor 20. Thus, a boundary of the sampling cavity 34 may be defined, in part, by a portion of the sensor 20 upon placement of the sensor 20 into the sensor housing 18. In one or more embodiments, the interface between the sensor 20 and the sensor housing 18 may comprise a membrane or other resilient seal for ensuring the connection, or interface, between the sensor 20 and the sensor housing 18 is water and air tight so as to enable an accurate measurement of characteristics and/or properties of the fluid in the sampling cavity 34. As depicted in FIG. 5, for example, the sampling cavity 34 may define an aperture 46 configured for receiving a portion of the sensor 20. The aperture may be circular, square, triangular, hexagonal, oval, or any other suitable shape.

As depicted in FIGS. 9-13, one or more exemplary embodiments of the sensor housing comprise a tapered first end 30 defining a first receiver 30' configured for receiving an infusion set tube 38, wherein the first receiver 30' defines a substantially planar base portion 50 and a cylindrical sidewall 52 upstanding therefrom, the base portion 50 defining a first, or upper, aperture 54. Alternatively, the first end may not be tapered and/or the sidewall may comprise a shape other than cylindrical without departing from the scope of the present disclosure. As described above, the tube 38 may be removably connected to the first receiver 30' via any suitable connecting means, or may alternatively be permanently affixed to or integral with the first, or upper, end 30 so as to form a unitary infusion set comprising a patient interface, a sensor housing, and a tube or other fluid delivery means affixed therebetween as depicted in FIG. 1B.

As depicted in FIGS. 11-13, one or more embodiments comprise first 40, or upper, and second 42, or lower, internal channels in fluid communication with the first receiver 30 via the first, or upper, aperture 54. Each internal channel may have a uniform diameter along its length. Alternatively, the internal channels may have non-uniform diameters. In one or more embodiments, the diameter of the first internal channel 40 is greater than the diameter of the second internal channel 42. Alternatively, the diameter of the first internal channel 40 is less than or equal to the diameter of the second internal channel 42. The first and second channels may be linear or nonlinear. In one or more embodiments, a sampling chamber 34 is positioned between the first and second internal channels, wherein the sampling chamber 34 is defined by a planar surface 62 having a cylindrical sidewall 64 projecting therefrom, wherein an edge of said circular sidewall 64 defines a second aperture 46 configured for receiving a portion 20' of a sensor 20. In one or more embodiments, the sidewall may comprise a shape other than cylindrical, such as square or any other suitable shape without departing from the scope of the present invention. The sidewall of the sampling chamber may also be non-planar without departing from the scope of the present disclosure. In one or more embodiments, the sidewall may be smooth, grooved, or textured.

In one or more embodiments, an external sensor compartment 36 configured for receiving the sensor 20 may be provided, wherein the external sensor compartment 36 is in fluid communication with the sampling chamber 34 via the second aperture 46. Internal sensor compartments are also envisioned. In the embodiments depicted in FIGS. 11-13, the second aperture 46 is oriented orthogonally to the first, or upper, aperture 54. Other angular orientations between the first and second apertures, however, are within the scope of the present disclosure. Thus, in one or more embodiments, the angular relationship between the first and second apertures is less than 90 degrees. Alternatively, the angular relationship between the first and second apertures may be greater than 90 degrees.

In one or more embodiments, an intermediate portion defining a coupling 28 for removably connecting the sensor housing 18 to a wire housing 26 may be provided, wherein the coupling 28 defines a pair of detents 28' for engaging corresponding slots in the wire housing 26. As will be apparent to one of ordinary skill in the art having the benefit of the teachings of the present disclosure, alternative means for connecting the sensor housing to the wire housing are within the scope of the present disclosure.

With continued reference to FIGS. 11-13, one or more embodiments comprise a second end 32 configured for engaging a pump system 12, wherein the second end 32 defines a second substantially planar base portion 70 and a second cylindrical sidewall 72 extending therefrom. In one or more embodiments, the second base portion 70 defines a third, or lower, aperture 74. The third aperture 74 may be parallel to the first, upper, aperture 54. Alternatively, the third aperture 74 may be angled relative to the first aperture 54 without departing from the spirit and scope of the appended claims. In the embodiments depicted in FIGS. 11-13, the second aperture 46 is oriented orthogonally to the third, or lower, aperture 74. Other angular orientations between the second 46 and third 74 apertures, however, are within the scope of the present disclosure. Thus, in one or more embodiments, the angular relationship between the second and third apertures is less than 90 degrees. Alternatively, the angular relationship between the second and third apertures may be greater than 90 degrees.

In the exemplary embodiment depicted, a needle 44 is shown protruding from the third, lower, aperture 74. In one or more embodiments, the needle 44 does not extend beyond the lower connector portion 32 of the sensor housing 18. However, embodiments wherein the needle 44 extends beyond the lower connector portion 32 of the sensor housing 18 are considered to be within the scope of the present disclosure. In one or more embodiments, attaching the second end 32, or lower connector portion, to the pump system 12 results in the needle 44 piercing a pump system reservoir 14, which contains a fluid, thereby enabling the flow of fluid from the pump 12 to the sensor housing 18, and ultimately through the sensor housing 18 to the infusion set 16 affixed to a subject.

One or more embodiments of the present disclosure include a sensor housing comprising a tapered first end defining a first receiver configured for receiving an infusion set tube; the first receiver having a substantially planar base portion and a cylindrical sidewall upstanding therefrom, the base portion defining a first aperture; first and second internal channels in fluid communication with the first receiver via the first aperture, each internal channel having a uniform diameter along its length, wherein the diameter of the first internal channel is greater than the diameter of the second internal channel; a sampling chamber positioned between the first and second internal channels, the sampling chamber defined by a planar surface having a cylindrical sidewall projecting therefrom, an edge of said cylindrical sidewall defining a second aperture configured for receiving a portion of a sensor; an external sensor compartment configured for receiving the sensor, the external sensor compartment in fluid communication with the sampling chamber via the second aperture; a second end configured for engaging a pump system, the second end defining a second substantially planar base portion and a second cylindrical sidewall extending therefrom, the second base portion defining a third aperture, a needle protruding from the third aperture; and an intermediate portion defining a coupling for removably connecting the sensor housing to a wire housing, the coupling having a pair of detents for engaging the wire housing, wherein attaching the second end to the pump system results in the needle piercing a pump system reservoir.

One or more embodiments of the present disclosure include a sensor housing, comprising: a first receiver configured for receiving an infusion set tube; first and second internal channels in fluid communication with the first receiver; a sampling chamber positioned between the first and second internal channels, the sampling chamber defining an aperture configured for receiving a portion of a sensor; and a second receiver configured for engaging a pump system; wherein attaching the second receiver to the pump system results in fluid flow between the sensor housing and a pump system reservoir.

Figure 14:
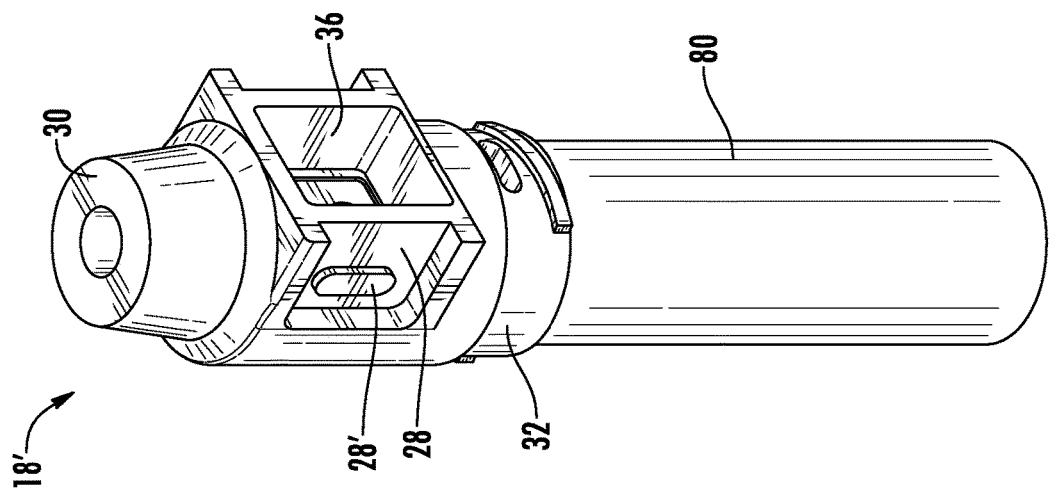
FIG. 14 depicts an alternate exemplary sensor housing.

FIG. 14 depicts an alternative embodiment of a sensor housing 18' having an integrated fluid reservoir. This embodiment of the sensor housing 18' comprises an extended lower portion 80 configured for housing at least one of a fluid and a fluid reservoir therein. Alternatively, the lower portion 80 comprises the reservoir. The extended lower portion 80 is operably connected to, and configured for connecting to, a suitable pump system for delivering the fluid in the reservoir through the sensor housing to a subject as herein described in connection with the various embodiments. In another embodiment, a fluid reservoir may have tubing that extends out of the reservoir and constitutes a portion of the flow path. As part of this flow path, there may be a sensor which may be connected in a similar fashion as in FIG. 13 with a sampling chamber somewhere along the tubing that is connected at either side with a fluid path of equal or different diameters which would connect directly to a cannula. The sampling chamber may be connected to a sensor as herein described. In one or more embodiments, the reservoir is an integral part of the pump with all the tubing internal to the device (tubeless/patch insulin pumps). In yet another embodiment, the reservoir flows directly into the sensing cavity, which is in fluid communication with an infusion set, via a luer-lock system or other connector, that is connected to the patient. In yet another embodiment, the reservoir, sensor housing, and infusion tubing constitutes one infusion set.

Exemplary "Smart" Infusion Set

As described hereinabove, and as depicted in FIG. 1B, one or more embodiments of the sensor housing may comprise a first, or upper, connector portion integrally connected to a tube associated with an infusion set. Therefore, one or more embodiments of the present disclosure may include an infusion set comprising a patient interface, said patient interface configured for being removably attached to the patient's skin and delivering a fluid to the patient; a sensor housing in fluid communication with the patient interface; and a tube positioned between the patient interface and the sensor housing. Tubeless embodiments are also envisioned, wherein the sensor housing and patient interface comprise a unitary structure.

In one or more embodiments, the sensor housing comprises any one of the various embodiments of a sensor housing disclosed herein. For example, the sensor housing may comprise a first connector portion configured for connecting the sensor housing to the patient interface via a tube; a second connector portion configured for connecting the sensor housing to a pump; a sampling cavity positioned between the first connector portion and the second connector portion, wherein the sampling cavity is in fluid communication with the first and second connector portions via first and second channels, respectively, and wherein said first and second channels provide a path for at least one needle, respectively; and a sensor chamber in fluid communication with the sampling chamber, said sensor chamber configured for accommodating a sensor, wherein said sensor measures a value associated with said fluid in said sampling cavity.

Exemplary Electronics Module/Kit

Referring again to FIGS. 1-3, an exemplary electronics housing, or kit 22, is illustrated, which includes a housing configured to store the electronic components used to detect infusion set malfunctions. This housing 22 may interact with the sensor housing 18 at the top or other portion thereof via a conductive material (i.e. gold plates, pins, etc.). In one or more embodiments, the housing is configured to clip onto, or cradle, the pump. Alternatively, the housing 22 may be in the form of a sleeve wherein the pump 12 is held, a clamp which engages at least one side of the pump 12, or a clip placed in line between a pump 12 and an infusion set 16. In one or more embodiments, the kit 22 may be independent from the pump and comprise a kit 22 configured for being placed in a location separate from the pump. The electronic components contained within the housing may comprise a microprocessor (not shown) for at least one of receiving, monitoring, and analyzing data received from the sensor, and a battery (not shown) for providing power to the sensor and other components of the system. The battery may or may not comprise a rechargeable battery. An internal antenna (not shown) for transmitting data from the kit 22 to an external device may also be provided.

In one or more exemplary embodiments, an nRF52 microcontroller uses its 3.3V regulated output to energize a Amphenol NPC-120 Wheatstone bridge based pressure sensor. The output from the sensor is fed to an Analog Devices AD623 instrumentation amplifier which boosts the signal by ~34 gain and feeds a signal back to the nRF52 ADC. The ADC input is converted to a psi reading for data acquisition.

In one or more embodiments, the power is turned on and the boot process initializes an SD card and creates a new file with a time stamp from the Real Time Clock "RTC". The main loop begins and records pressure data on 1 second intervals. The normal state of the prototype is to take a 1 hour rolling average of the basal (steady medication flow) pressure. If a bolus (large volume injection) event is started on the pump, a button on the system is pressed until a beep is heard, then the monitoring event is flagged as "bolus" and the basal rolling average is paused until the bolus event is over. The bolus can be ended with a second button press, or a pressure curve monitoring algorithm. If a pressure (or other) reading is outside of the preset parameters during a bolus event, an alarm will sound. There is also a pressure alarm for basal monitoring. Alternatively, the system may require no pressing of any buttons to identify a delivery event and can detect fluid delivery. In one or more embodiments, the system will actively read basal pressure rates and monitor for any sensor readings outside of the acceptable parameters. If sensor readings are outside parameters, this will trigger a notification/alert to the user and/or 3rd party. In another embodiment, this alert system can detect any type of issue/malfunction including, but not limited to, a leak at the infusion site, block at the infusion site, a block in the infusion set, a malfunction of the pump, a kink in the infusion set cannula, a dislodgment of the cannula, any hypertrophic, damaged or inflamed tissue associated with the infusion/injection site, based on the interpreted pressure readings.

Exemplary Methods for Detecting System Malfunctions

Figure 15:
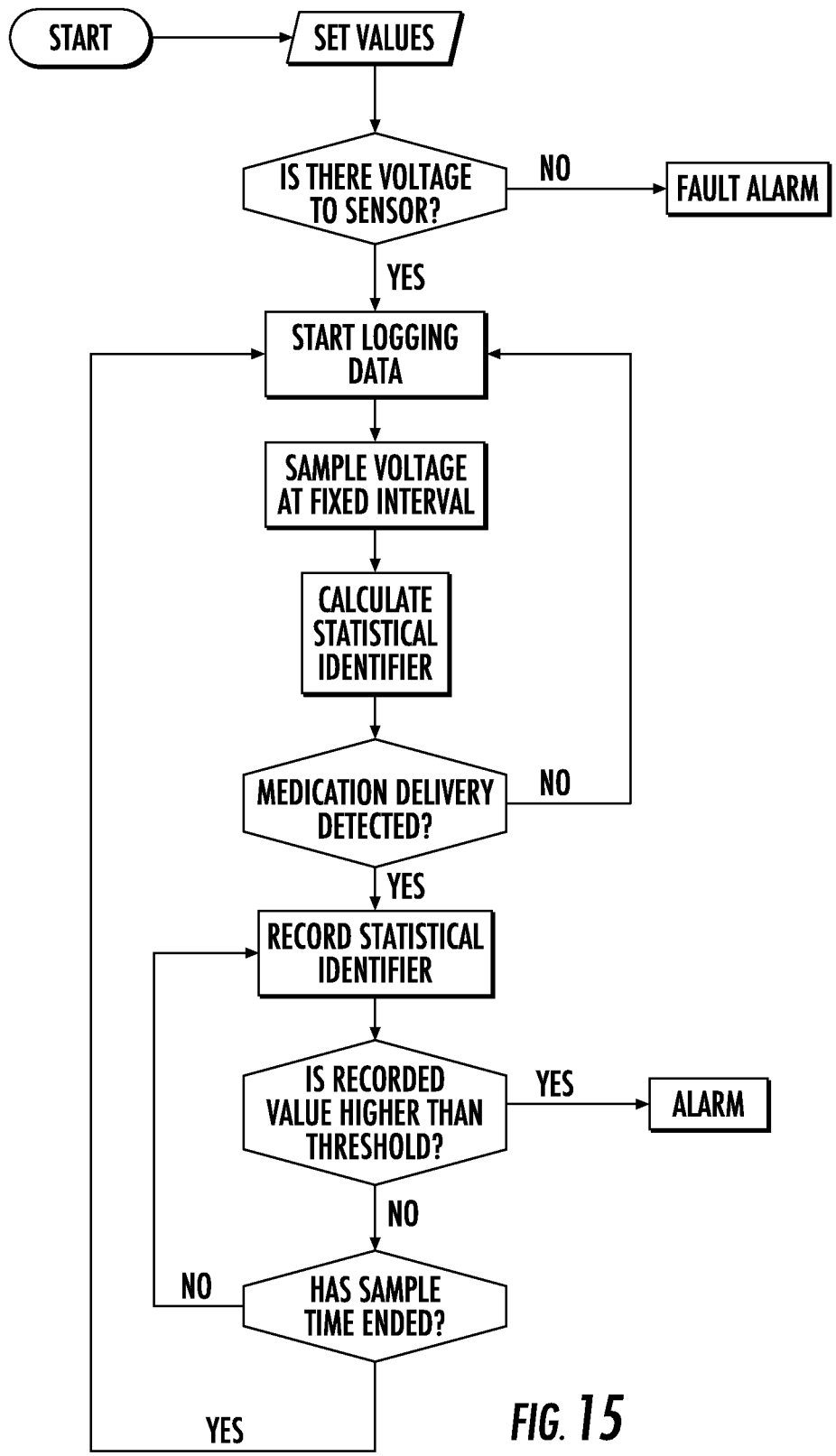
FIG. 15 depicts a flow chart of a method for detecting one or more malfunctions in an infusion pump in accordance with one or more embodiments of the disclosed technology.
Figure 16:
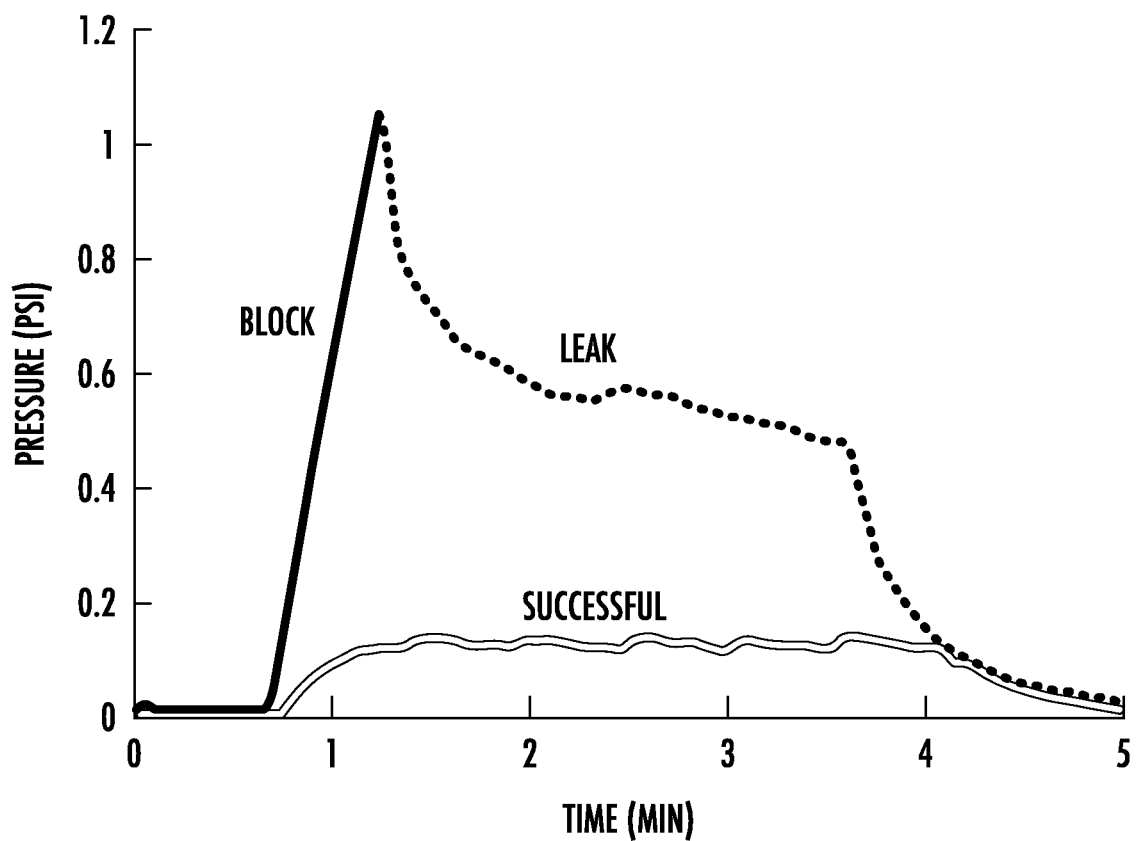
FIG. 16 depicts exemplary data provided in accordance with systems and methods of the present disclosure.

FIG. 15 depicts on exemplary method in accordance with the teachings of the present disclosure. One or more embodiments comprise a method for detecting malfunctions in a fluid delivery system. Alternatively, one or more embodiments comprise a method for detecting viability of injection sites not only for insulin injections, but any form of medication which requires medicine diffusing into a patient intradermally or subcutaneously. At the start, the system may accept input values from past evaluations. These values may include but are not limited to tolerable tissue back pressure, diffusion rate associated with back pressure, flow approximation, a max value of the tissue back pressure, a minimum value of tissue back pressure, the rate of change associated with medication delivery (i.e. rate of pressure change), the average of any of these values, or a percent deviation from any of these values. These values may be inputted by a user, such as, for example, a patient's endocrinologist or the manufacturer of the system during the manufacturing process of the device. Alternatively, these inputted values may change over time based on the user's historical data, variations in treatment, or suggested alternatives from the system better personalized to the individual's anatomical, biochemical, or pharmacological variations throughout the use of the device. Inputted values may be altered or reset by a user, physician, or manufacturer to best address the needs of the patient. After values have been inputted and the system is "on," the device may identify whether there is a clear power reading coming from the sensor. This may be in the form of an electrical reading (i.e. voltage, mA, etc.), an auditory signal, tactile signal, and/or manual confirmation. In one or more embodiments, the system may assess the sensor's length of use (duration of time since initial use) and determine whether or not to accept the use of said sensor system.

If the system is operating as intended (i.e. sensor is connected and viable) the path may continue to the next block. If the system is not operating as intended, then a fault alarm may occur. This alarm may be, but is not restricted to, a visual indicator, audio indicator, tactile indicator, Bluetooth™ notification, radio transmission (i.e. phone call, text), a transmittable message to an internet of things (IoT) device or other suitable alarm or alert.

After the system has been initialized, the system may take in values at a predetermined rate (i.e. 1 second, 5 seconds, etc.). The values can be any one or more of the ones listed above (i.e. electrical, tactile, audible, etc.). These readings may undergo an analysis which will determine values of interest (i.e. max pressure, min pressure, average pressure, etc.). With the values detected, the system may decide whether a predetermined amount of fluid, such as insulin or any other medication, has been delivered and/or is being delivered. In another embodiment, the values detected lead to the system deciding whether or not it is to the benefit of the user to inject the medication delivery device into the same infusion/injection site or body region associated with site and may suggest another body region associated with infusion/injection sites to be utilized. This functionality may be used to assess and map viable/unviable injection/infusion sites. Thus, one or more embodiments of the systems and methods described herein may be used to provide a map of viable and non-viable injection sites on a user.

If no bolus or other defect/malfunction in the delivery of the fluid is detected, the system may remain in its data sampling mode. Otherwise, the system may initialize the next block. When the system enters this next loop, it may begin calculating values of interest. These values may include but are not limited to average pressure reading, max pressure reading, min pressure reading, estimated fluid flow, value rate of change, or duration. If the values found/calculated are higher than acceptable an alarm may be triggered. This alarm may be in the forms listed above (i.e. audible, Bluetooth™, visual, tactile, etc.). If no value is found to be outside of its accepted amount, the system may assess if enough time has passed or if the value found are within a "safe" range, e.g. within an acceptable tolerance, such as a set standard deviations calculated from historical user data or defined by physician or manufacturer. If yes, then the system may return to its data logging mode. As used herein, "value/values" refers to any number or calculated amount determined by the system or number assigned to any electrical, tactile, audible, or frequency identified by the system.

Thus, one or more embodiments of the present disclosure comprise a method for monitoring characteristics of a fluid being delivered and detecting abnormalities within an infusion set and at an infusion site, the method comprising:

(i) inputting base values into a processor, said base values comprising at least one of a tolerable back pressure, a diffusion rate associated with said back pressure, a flow rate approximation, a maximum permissible back pressure, a minimum permissible back pressure, a rate of pressure change, and a percent deviation of the same;

(ii) identifying a presence of a voltage to a sensor, wherein the presence of a voltage initiates a logging of data, and wherein the absence of a voltage triggers an alarm;

(iii) logging data at a predetermined interval; said logging comprising sampling the voltage to the sensor at a predetermined interval;

(iv) calculating, by the processor, a statistical identifier associated with a value of interest, said value of interest selected from the group consisting of maximum pressure, minimum pressure, and average pressure;

(v) determining, based on the statistical identifier, a medication delivery event, wherein a negative medication delivery event triggers the system to return to the logging step, and wherein a positive medication delivery event triggers the system to record a statistical identifier; and (vi) determining, by a processor, whether the statistical identifier is greater than or less than a predetermined threshold (such as, in one or more non-limiting exemplary embodiments, a range or standard deviation from a predetermined value), wherein if the statistical identifier is outside an acceptable predetermined threshold, the system triggers an alarm, and wherein if the statistical identifier is within the predetermined threshold, determining, by a processor, whether a sample time has ended.

One or more embodiments of the present disclosure may also comprise:

(i) pairing an infusion set or other medication delivery device with a mobile app via BLE, radio frequency, or Wi-Fi;
(ii) initiating a calibration sequence with no medication flowing through line;
(iii) entering an infusion site location on a mobile app;
(iv) measuring, with a sensor, data from a fluid channel (before, during, and after medication flow has begun);
(v) sending data from the sensor to a microcontroller (continuously or after being prompted by the user);
(vi) analyzing, by the microcontroller, the data and deciding if an infusion process is normal or abnormal; wherein if normal, repeating at least one of the prior steps, and wherein if abnormal, alerting, by the microcontroller or some other alarm delivery device, the user through an auditory, visual, or haptic signal;
(vii) sending, by the microcontroller or other transmitter, information to the mobile device application through Bluetooth™ or other communication technology.

In one or more embodiments, a mobile device application will store infusion data relating to performance of said infusion site, including but not limited to where abnormal infusions are occurring on the patient's body and be able to suggest better infusions sites for patient to use. In one or more embodiments, a mobile app will connect to the microcontroller or other component in the electronic kit housing and will alert the patient and/or a caregiver of injection site malfunctions through SMS message or Push Notifications. In another embodiment, the sensor housing stores the infusion data and the mobile app connects with the sensor housing electronics in order to alert patient to malfunctions.

One or more embodiments of the present disclosure may also comprise (i) turning on the sensor system;
(ii) detecting, with the system, no medication flow and initiating a calibration sequence;
(iii) receiving, by the sensor, data from a fluid channel (before, during, and after medication flow has begun);
(iv) sending, by the sensor, data to a microcontroller (continuously or after being prompted by the user);
(v) analyzing, by the microcontroller, the data and deciding if infusion process is normal or abnormal, wherein if normal, repeating at least one of the prior steps, and wherein if abnormal, alerting, by the microcontroller or other alarm delivery device, the user through an auditory, visual, or haptic signal;
(vi) logging and/or storing data at various intervals; and
(vii) exporting the data to a physician or other third party for evaluation.

In one or more embodiments, a sensor reading is used to at least one of estimate or calculate absorption of fluid delivered intradermally or subcutaneously. Absorption estimates and/or rates may be used to estimate the amount of insulin received by the user/patient, identify leaks, identify occlusions, identify infusion site problems, assess infusion site status, identify cannula dislodgement, and identify and/or assess a user's active state (i.e. whether the user is exercising or has an elevated heart rate).

Exemplary parameters measured by the system may include, but are not limited to, full width at half maximum value, maximum value, minimum value, average value, moving average, median value, slope, area under a curve, regression, time to peak, and time to rise.

In one or more embodiments, the TCP protocol comprises:

(i) measuring pressure with the fluid line empty of any liquid, wherein a measured pressure may be considered the atmospheric pressure reading (baseline reading);
(ii) measuring a pressure of the fluid during priming of the line (air pressure) and establishing baseline line pressure with fluid;
(iii) measuring a pressure of fluid during infusion into tissue (infusion pressure); and
(iv) calculating TCP by taking the difference of infusion pressure, air pressure, and atmospheric pressure (TCP=Infusion Pressure−In-line Pressure (priming pressure)−Baseline Pressure (Atmospheric).

In one or more embodiments, a protocol for identifying a health of medium and identity of medium comprises the following definitions:

Healthy Site: A site where normal use has been classified and has minimal failure percentage and can be classified through CGM data;

Unhealthy Site: A site where normal use has been characterized and current performance is outside of acceptable tolerance (may require historical patient data to classify or large data set) and can be classified through CGM data;

Good Site: Site with low failure percentage (may require patient data for this demarcation);

Bad Site: Site with high failure percentage (may require patient data for this demarcation);

Difference between Unhealthy Site and Bad Site: Unhealthy has been classified as such due to historical patient data and "Normal/Healthy" has been characterized, Bad-Site is a site with a high rate of failure.

In one or more embodiments, a method for data acquisition for a new patient comprises:

(i) at least one of checking a sensor status, a functionality, and pairing with a device;
(ii) pre-loading manufacturer limits for failure (extreme failure limits determined through clinical trials, experimentation, or other)
(iii) establishing baseline infusion set measurements (no fluid and primed);
(iv) choosing an infusion site;
(v) initiating injection into the infusion site;
(vi) recording an injection profile;
(vii) establishing baseline measurements from site;
(viii) determining if site is within an operational tolerance (no initial kink or block) [may require waiting period before bolus];
(ix) allowing a waiting period;
(x) detecting bolus entered into pump;
(xi) registering, by the system, the bolus via connection to pump and/or determination of flow via statistical identifier;
(xii) logging data for inputted site, wherein if bolus is finalized without any failure or warning, logging as successful bolus; and wherein if bolus is finalized with a failure or readings outside of acceptable preloaded tolerances, have user examine site and flag;

(xiii) repeating monitor and detection steps for entirety of use period, wherein if site fails throughout use period, flag failure, flag site, and record failure statistical identifiers (time to peak, max, min, FWHM, etc.), and wherein if site does not fail throughout use period, log as successful site and record statistical identifiers (time to peak, max, min, FWHM, etc.).

In one or more embodiments, a method for site mapping for a long-term user comprises:

(i) at least one of checking sensor status, functionality, and pairing with device;

(ii) loading manufacturer limits for failure (extreme failure limits determined through clinical trials, experimentation, or other) corrected using historical patient data;

(iii) establishing baseline infusion set measurements (no fluid and primed);

(iv) choosing an infusion site;

(v) injecting into infusion site;

(vi) logging and analyzing cannula injection profile;

(vii) establishing baseline measurements from site;

(viii) determining if site is within operational tolerance (no initial kink or block) [may require waiting period before bolus]

(ix) allow a waiting period;

(x) entering bolus into pump;

(xi) registering bolus via connection to pump and/or determination of flow via statistical identifier;

(xii) beginning data logging for inputted site;

(xiii) monitoring bolus and analyzing using historical statistical identifier for specific site, wherein if within acceptable tolerance, do nothing and continue to record statistical identifier for current use period, and wherein if not within acceptable tolerance, flagging bolus event and comparing to other sites, wherein if outside of tolerance for chosen site and other sites, notifying user and recommending a new site;

(xiv) changing flag to potential bad site, wherein if adverse event occurs through wear time (failure like kink or leak or blood glucose grossly outside tolerance), marking as failed site (xv) logging data for failure type and failed site, wherein if fail percentage is above x %, flagging as bad site and avoiding use, and wherein if fail rate is determined to be because of user error (dislodgement or environmental error) flagging site as such, but do not record failure data.

In one or more embodiments, a healthy site will have low failed use periods and tolerable blood glucose levels. Likewise, an unhealthy site may involve poor infusion profiles at the edge of tolerance and possibly poor blood glucose levels. In one or more embodiments, thresholds of tolerances (optimal, acceptable, borderline {unsuccessful bolus y % of the time but not as bad as z % of the time x %>y %<z %}, and outside of tolerance}). Historical data sets for each patient may aid in finding what unhealthy sites are like, characterize them, and pre-load values into device for evaluation.

Having thus described preferred exemplary embodiments of the technology, advantages can be appreciated. Variations from the described embodiments exist without departing from the scope of the claims. For example, fluid pressure sensing could be incorporated into the reservoir of the pump or directly at the infusion site. Another embodiment may comprise inserting a membrane inside the sensor housing that can deform with fluid pressure, wherein the deformity can be correlated to a fluid pressure reading.

Any material that is biocompatible can be used as the sensor housing material, such as a polymer like polycarbonate. The conductive plate used to provide power to the sensor housing from the electronic kit can be made of any suitable conductive material. The placement of the electronic kit can be adjacent to the sensor housing as opposed to on the back of the insulin pump. The sensor could eventually become part of the blueprint of future insulin pump models and can easily be incorporated within the electronics and housing of the pump. Thus, it is seen that apparatus and methods are provided for detecting one or more malfunctions related to an infusion pump.

Although particular embodiments have been disclosed herein in detail, this has been done for purposes of illustration only, and is not intended to be limiting with respect to the scope of the claims, which follow. In particular, it is contemplated by the inventors that various substitutions, alterations, and modifications may be made without departing from the spirit and scope of the technology as defined by the claims. Other aspects, advantages, and modifications are considered to be within the scope of the following claims. The claims presented are representative of the technology disclosed herein. Other, unclaimed technology is also contemplated. The inventors reserve the right to pursue such technology in later claims.

Exemplary, non-limiting, modifications to one or more of the embodiments disclosed herein may include placing the sensor and/or sensor housing anywhere along the fluid path, such as, for example, connected to the reservoir or placed inside the pod portion (i.e. patient interface) of an infusion set near the infusion site. Alternatively, the sensor could be imbedded into the infusion pump, so it has contact with reservoir. The sensor could also be imbedded into the pod portion of an infusion set close to the needle injector and tubing connector.

In one or more embodiments, the sensor could be imbedded into "patch pumps" as long as it is in contact with the fluid line. The sensor could be imbedded into an injection pen close to the tip of the injector as long as it is contact with some type of fluid.

In one or more embodiments, the tubing material could be a material that expands and contracts with medication flow, wherein a deformation of the tubing triggers an electrical signal which can be read, interpreted, and used to evaluate medication flow.

In one or more embodiments, the microcontroller could be placed in a housing that connects to any point on the external part of an infusion pump. The microcontroller may be in a standalone box that does not have any connecting wires. In another embodiment, the microcontroller may be in standalone box that has one wire that connects to an electrical outlet. In yet another embodiment, the microcontroller may be placed inside the infusion pump, thereby eliminating the need for an external attachment (i.e. electronics kit).

In one or more embodiments, the sensor could be directly connected to a microcontroller through the use of wires. Alternatively, the sensor could connect to a microcontroller through use of Bluetooth Low Energy (BLE). In yet another embodiment, the sensor can connect to the microcontroller via fiber optic cable, conductive plate, or conductive gel to relay data. In another embodiment, the sensor and microcontroller could be part of the same electric board inside the sensor housing. In yet another embodiment, the sensor, microcontroller, and infusion pump circuitry can be part of the same electric board.

In one or more embodiments, the microcontroller may connect to a mobile device through the use of Bluetooth Low Energy (BLE). Alternatively, the microcontroller could connect to a mobile device through the use of Wi-Fi or radiofrequency. In yet another embodiment, the mobile device may be connected through BLE, Wi-Fi, or radio frequency and the data is sent in data sets through an internet portal. Data may be sent continuously or on demand by the user.

In one or more embodiments, the sensor could be used to measure pressure in the fluid line or a rate of fluid infusion. Sensing may also be done through an electrical chemical change. Tactile sensing may also be incorporated to evaluate when the pump is operational and flowing medication. There may also be a sound sensor which registers the audible noise from the pumps motor and uses it to evaluate flow. Another embodiment may comprise inserting a membrane inside the in-line fluid sensor that can deform with fluid pressure, and the deformity can be correlated to a fluid pressure reading.

Any material that is biocompatible can be used as the housing material, such as polycarbonate. Different types of sensors configured for measuring pressure, flow rate, humidity, temperature, ultrasound, impedance, ion levels, etc. are also within the scope of the present disclosure.

In one or more embodiments, the data from the sensor may be stored on an external storage device such as, for example, a microSD card within the microcontroller system. The data may also be sent to cloud storage where it could connect to a data storage server and be encrypted for security purposes. The data may also be sent to health data cloud services that are currently in the market, such as Glooko, through the internet. Data may also be stored on a paired electronic device (i.e. smartphone, etc).

The sensor may be powered through the use of wires to an external battery near the microcontroller. If the electronics kit is independent (not directly connected) of the sensor, then the infusion set can be connected to a power source via conductive plate (metal, chemical, etc.) to supply power to sensor. A battery may be included in the sensor housing to provide power directly to sensor. The sensor may also be powered by a battery that converts mechanical movement of patient into electrical power. The sensor may also be powered by a detachable battery separate from the electronics housing which connects via magnets, conductive plates, or cables and can charge by directly connecting to the sensor or via induction charging. In one or more embodiments, the sensor may be powered by the energy of the infusion pump itself.

The microcontroller may be powered by a battery on the same circuit board inside the housing that is connected to the back of the infusion pump. The microcontroller may be powered by an electrical outlet if it was a part of standalone box. The microcontroller may be powered by a battery that converts mechanical movement of patient into electrical power. Microcontroller may be powered by infusion pump itself.

The embodiments disclosed herein may be utilized with many different types of infusion pumps, including but not limited to, those used for treating diabetes, cancer, pregnancy, and delivering IV medication. The algorithms disclosed herein may be integrated into future infusion pump software. Embodiments herein may be used with multi-medication infusion pumps (i.e. a pump that dispenses at least two medications via at least two infusion sets or dual chamber tube; pumps that dispense more than one medication without external tubing like Omnipod). The embodiments disclosed herein are not limited to the use of external tubing, and may also be used in connection with internally-housed medication dispensing pumps. Embodiments herein may be utilized at the same infusion site as continuous glucose monitors (CGMs) in-line with the medication fluid. Embodiments herein may be utilized with stationary or ambulatory infusion pumps. Alternatively, embodiments herein may be integrated with injection pens, syringes, and the like as they inject a fluid into intradermal or subcutaneous tissue.

It is accordingly intended that all matter contained in the above description or shown in the accompanying drawings be interpreted as illustrative rather than in a limiting sense. It is also to be understood that the following claims are intended to cover all of the generic and specific features of the technology as described herein, and all statements of the scope of the technology which, as a matter of language, might be said to fall there between.

Although the invention has been described relative to various selected embodiments herein presented by way of example, there are numerous variations and modifications that will be readily apparent to those skilled in the art in light of the above teachings. It is to be understood that, within the scope of claims supported by this specification, the invention may be practiced other than as specifically described.

What is claimed is:

1. A system for monitoring characteristics of a fluid being delivered and detecting abnormalities at an infusion site, the system comprising:
   an infusion pump configured for delivering a fluid;
   at least one sensor configured to generate output signals corresponding to at least one fluid characteristic;
   a processor in communication with the at least one sensor, and configured to:
      detect abnormalities in delivery of the fluid based on the output signals from the at least one sensor, at least one predetermined baseline value regarding an amount of fluid to be delivered to the user, and an error threshold; and
      generate outputs corresponding to said detected abnormalities and comprising an identified suitable reinjection site for the user based at least in part on historical fluid delivery data for the user.

2. The system of claim 1, wherein the processor is configured to detect abnormalities based on detected changing conditions along a flow path, said changing conditions indicative of fluid delivery failure, and detected via at least the output signals from the at least one sensor.

3. The system of claim 1, wherein the at least one sensor is configured to generate output signals corresponding to an absorption rate of the fluid at the infusion site.

4. The system of claim 1, wherein at least one of the at least one sensor is integrated with the infusion pump.

5. The system of claim 1, wherein at least one of the at least one sensor is associated with an infusion set coupled to the infusion pump and terminating at the infusion site.

6. The system of claim 5, wherein the infusion set is associated with a continuous glucose monitor at the same infusion site.

7. The system of claim 1, wherein the processor is further in communication with a mobile computing device via a wireless communications network, and wherein the outputs generated by the processor are provided as alerts for display on the mobile computing device via a mobile application associated therewith, wherein the mobile application is configured to analyze the alerts from the processor and to determine a recommended different infusion site for the user.

8. The system of claim 1, wherein the sensor is selectively coupled between the infusion pump and an infusion set, the sensor residing in a sensor housing comprising:
   a first connector portion configured for connecting the sensor housing to the infusion set;
   a second connector portion configured for connecting the sensor housing to the infusion pump;
   a sampling cavity positioned between the first connector portion and the second connector portion, the sampling cavity in fluid communication with the first and second connector portions via first and second channels, respectively; and
   a sensor chamber in fluid communication with the sampling chamber, said sensor chamber configured for receiving the sensor.

9. The system of claim 8, wherein the sensor chamber extends orthogonally to a flow path of fluid through the first and second channels.

10. The system of claim 8, wherein the sensor is configured for at least one of collecting and transmitting data pertaining to at least one fluid characteristic of a fluid in the sampling cavity.

11. The system of claim 8, wherein a portion of the sampling cavity is defined by the sensor.

12. The system of claim 8, wherein the sampling cavity defines an aperture configured for receiving a portion of the sensor.

13. The system of claim 1, further comprising an infusion set comprising:
   an interface configured for being removably attached to the user's skin and delivering a fluid to the user; and
   a sensor housing in fluid communication with the interface, said sensor housing comprising:
      a first connector portion configured for connecting the sensor housing to the interface via a tube;
      a second connector portion configured for connecting the sensor housing to a pump;
      a sampling cavity positioned between the first connector portion and the second connector portions, the sampling cavity in fluid communication with the first and second connector portions via first and second channels, respectively; and
      a sensor chamber in fluid communication with the sampling chamber, said sensor chamber configured for receiving a sensor.

14. The system of claim 13, wherein the sampling cavity defines an aperture configured for receiving a portion of the sensor.

15. The system of claim 13, further comprising a needle extending from the second channel, wherein connecting the second connector portion to the pump results in the needle piercing a fluid reservoir in the pump, thereby enabling a flow of fluid from the reservoir to the infusion set.

16. A system for monitoring characteristics of a fluid being delivered and detecting abnormalities at an infusion site, the system comprising:
   an infusion pump configured for delivering a fluid;
   at least one sensor configured to generate output signals corresponding to at least one fluid characteristic;
   a processor in communication with the at least one sensor, and further in communication with a mobile computing device via a wireless communications network, wherein the processor is configured to
   detect abnormalities in delivery of the fluid based on the output signals from the at least one sensor, at least one predetermined baseline value regarding an amount of fluid to be delivered to the user, and an error threshold, and
   generate outputs corresponding to said detected abnormalities as alerts;
   wherein a mobile application associated with the mobile computing device is configured upon receiving an alert from the processor to
   identify a current injection site for the user,
   record the alert as corresponding to detected abnormalities with respect to the current injection site, and
   update accordingly a map comprising suitable and unsuitable injection sites for the user.

17. The system of claim 16, wherein at least one of the at least one sensor is associated with an infusion set coupled to the infusion pump and terminating at the infusion site, and wherein the infusion set is associated with a continuous glucose monitor.

18. A system for monitoring characteristics of a fluid being delivered and detecting abnormalities at an infusion site, the system comprising:
   an infusion pump configured for delivering a fluid;
   at least one sensor configured to generate output signals corresponding to at least one fluid characteristic;
   a processor in communication with the at least one sensor, and configured to:
      generate outputs corresponding to detected abnormalities in delivery of the fluid based on the output signals from the at least one sensor, at least one predetermined baseline value regarding an amount of fluid to be delivered to the user, and an error threshold;
      identify a presence of an electrical signal to the at least one sensor, wherein the presence of the electrical signal initiates a logging of data, and wherein the absence of the electrical signal triggers an alarm;
      log data at a predetermined interval, said logging comprising sampling the electrical signal to the at least one sensor at the predetermined interval;
      calculate a statistical identifier associated with a value of interest; and
      determine, based on the statistical identifier, a medication delivery event, wherein a negative medication delivery event triggers the processor to return to the logging step, and wherein a positive medication delivery event triggers the processor to record a statistical identifier.

19. The system of claim 18, wherein the processor is configured to:
   determine whether the statistical identifier is outside a predetermined threshold,
   wherein if the statistical identifier is outside the predetermined threshold an alarm is triggered via the outputs generated by the processor, and
   wherein if the statistical identifier is within the predetermined threshold a sample time is ended.

20. The system of claim 19, wherein at least one of the at least one sensor is associated with an infusion set coupled to the infusion pump and terminating at the infusion site, and wherein the infusion set is associated with a continuous glucose monitor.

* * * * *